United States Patent
Iwashita et al.

(10) Patent No.: US 12,217,401 B2
(45) Date of Patent: Feb. 4, 2025

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Atsushi Iwashita, Tokyo (JP); Kosuke Terui, Kanagawa (JP); Ryuichi Fujimoto, Tokyo (JP); Sota Torii, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 369 days.

(21) Appl. No.: 17/868,942

(22) Filed: Jul. 20, 2022

(65) Prior Publication Data

US 2022/0366543 A1    Nov. 17, 2022

Related U.S. Application Data

(63) Continuation of application No. PCT/JP2021/004897, filed on Feb. 10, 2021.

(30) Foreign Application Priority Data

Feb. 10, 2020   (JP) .................. 2020-020889
Feb. 10, 2020   (JP) .................. 2020-020892

(51) Int. Cl.
*G06K 9/00*    (2022.01)
*G06T 5/20*    (2006.01)
(Continued)

(52) U.S. Cl.
CPC .................. *G06T 5/70* (2024.01); *G06T 5/20* (2013.01); *G06T 5/50* (2013.01);
(Continued)

(58) Field of Classification Search
CPC .... G06T 5/70; G06T 5/20; G06T 5/50; G06T 2207/10116; G06T 2207/20192; G06T 2207/20224; G06T 2207/30008
See application file for complete search history.

(56) References Cited

U.S. PATENT DOCUMENTS 5,049,746 A  *  9/1991  Ito ........................ G06T 5/50
                                                378/98.12
5,123,054 A     6/1992  Hara et al.
(Continued)

FOREIGN PATENT DOCUMENTS

CN    107203983 A  *  9/2017  ........... A61B 6/5258
DE    102009010501 A1 *  9/2010  ........... G06T 11/005
(Continued)

OTHER PUBLICATIONS

Resolution enhancement in dual-energy x-ray imaging, Pierre Gravel* et al., Medical Imaging, 2005, pp. 614-624 (Year: 2005).*
(Continued)

*Primary Examiner* — Jayesh A Patel
(74) *Attorney, Agent, or Firm* — Venable LLP

(57) ABSTRACT

An image processing apparatus performs first noise reduction processing on a plurality of radiation images corresponding to mutually-different radiation energies, generates a decomposition image by energy subtraction processing using the plurality of radiation images obtained by performing the first noise reduction processing, and performs second noise reduction processing on the decomposition image, wherein the second noise reduction processing uses a filter that differs from a filter used in the first noise reduction processing in at least one of size and type.

20 Claims, 15 Drawing Sheets

(51) Int. Cl.
  *G06T 5/50* (2006.01)
  *G06T 5/70* (2024.01)
(52) U.S. Cl.
  CPC .......... *G06T 2207/10116* (2013.01); *G06T 2207/20192* (2013.01); *G06T 2207/20224* (2013.01); *G06T 2207/30008* (2013.01)

(56) References Cited

U.S. PATENT DOCUMENTS

| | | | |
|---|---|---|---|
| 5,402,338 A * | 3/1995 | Ito | G06T 5/75 600/407 |
| 5,966,468 A | 10/1999 | Fujimoto | |
| 7,068,826 B2 * | 6/2006 | Jabri | A61B 6/405 382/128 |
| 7,263,214 B2 | 8/2007 | Uppaluri et al. | |
| 11,422,098 B2 | 8/2022 | Iwashita et al. | |
| 11,430,161 B2 | 8/2022 | Iwashita et al. | |
| 2003/0095630 A1 * | 5/2003 | Avinash | A61B 6/4241 378/98.9 |
| 2003/0215119 A1 | 11/2003 | Uppaluri et al. | |
| 2004/0081280 A1 * | 4/2004 | Avinash | G06T 5/50 378/62 |
| 2008/0303952 A1 * | 12/2008 | Nakayama | H04N 5/21 348/607 |
| 2016/0213344 A1 | 7/2016 | Yi et al. | |
| 2020/0205755 A1 | 7/2020 | Iwashita et al. | |
| 2020/0211238 A1 * | 7/2020 | Iwashita | G06T 5/20 |
| 2020/0408704 A1 * | 12/2020 | Iwashita | A61B 6/4241 |
| 2020/0408933 A1 * | 12/2020 | Iwashita | H04N 5/3205 |
| 2022/0076415 A1 | 3/2022 | Tsukuda et al. | |
| 2022/0091050 A1 | 3/2022 | Iwashita et al. | |

FOREIGN PATENT DOCUMENTS

| | | | |
|---|---|---|---|
| JP | H03-133430 A | 6/1991 | |
| JP | H0-3263982 A | 11/1991 | |
| JP | 2004-000609 A | 1/2004 | |
| JP | 2010-005252 A | 1/2010 | |
| JP | 2014151009 A * | 8/2014 | |
| JP | 5634880 B2 * | 12/2014 | A61B 34/10 |
| JP | 2019-068952 A | 5/2019 | |
| JP | 2019-068953 A | 5/2019 | |
| JP | 2019-162358 A | 9/2019 | |
| WO | WO-2011091300 A2 * | 7/2011 | A61B 6/032 |
| WO | WO-2016168194 A1 * | 10/2016 | A61B 5/318 |
| WO | WO-2019069523 A1 * | 4/2019 | A61B 6/482 |
| WO | WO-2019181230 A1 * | 9/2019 | A61B 6/4233 |

OTHER PUBLICATIONS

A study on noise reduction for dual-energy CT material decomposition with autoencoder, Mohan Li et al., Springer, 2019, pp. 1-13 (Year: 2019).*

Apr. 13, 2021 International Search Report for International Patent Application No. PCT/JP2021/004897.

* cited by examiner

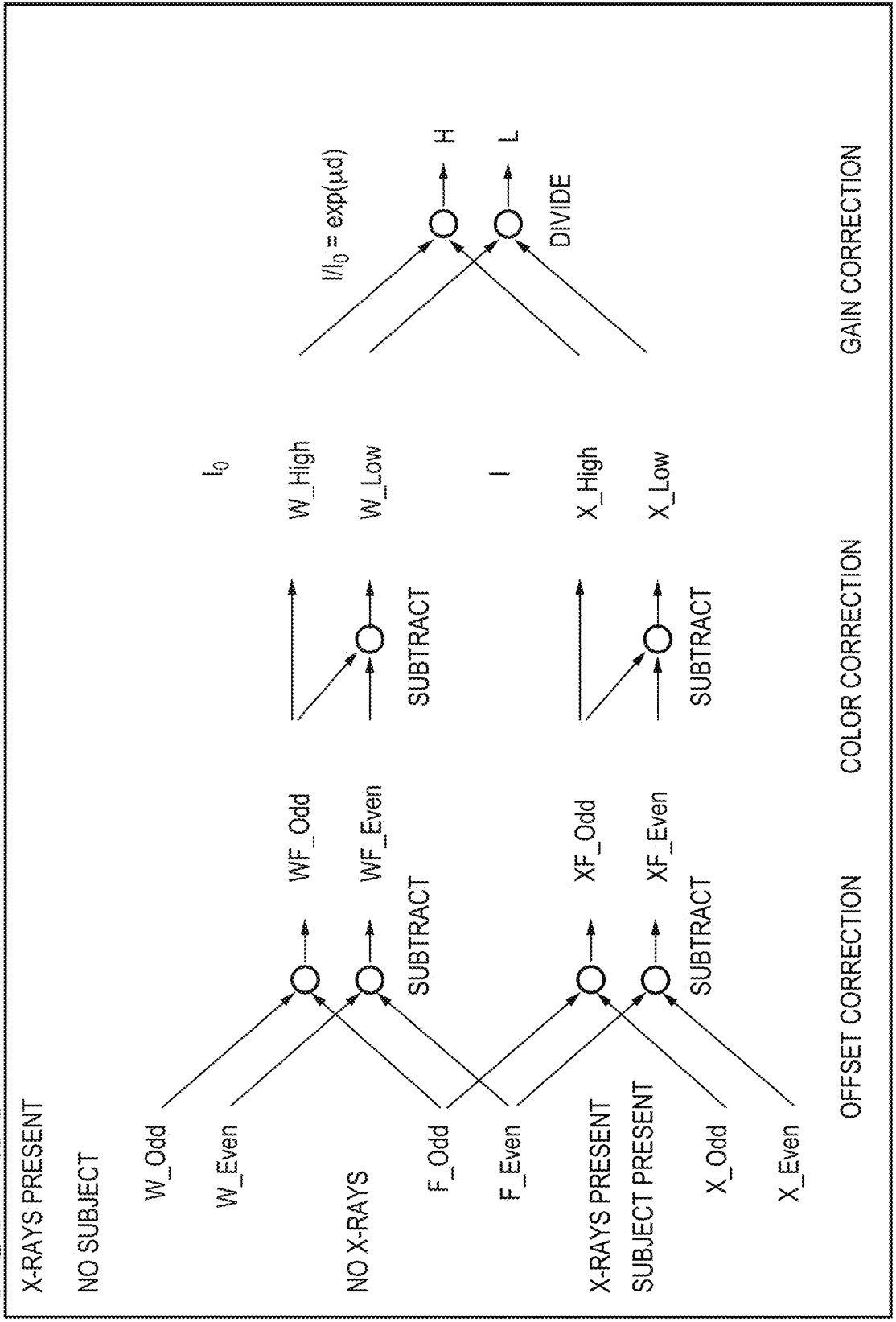

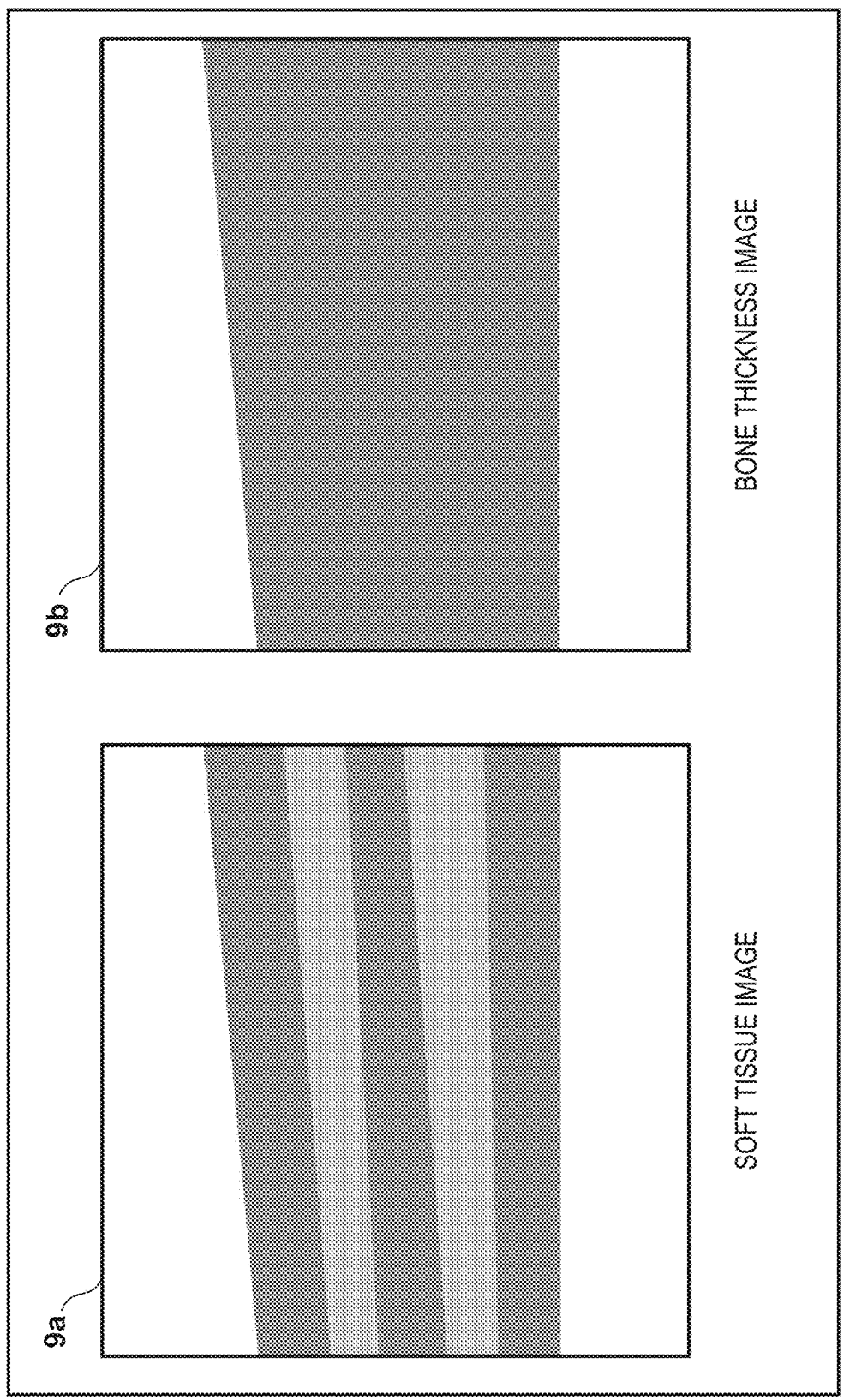

IMAGE PROCESSING APPARATUS, IMAGE PROCESSING METHOD, AND STORAGE MEDIUM

CROSS-REFERENCE TO RELATED APPLICATIONS

This application is a Continuation of International Patent Application No. PCT/JP2021/004897, filed Month Feb. 10, 2021, which claims the benefit of Japanese Patent Application No. 2020-020889, filed Feb. 10, 2020 and Japanese Patent Application No. 2020-020892, filed Feb. 10, 2020, all of which are hereby incorporated by reference herein in their entirety.

BACKGROUND OF THE INVENTION

Field of the Invention

The present invention relates to an image processing apparatus and an image processing method that process radiation images and storage medium.

Background Art

At present, radiographic imaging apparatuses using flat panel detectors (abbreviated as "FPDs" hereinafter) formed from semiconductor materials are widely used as imaging apparatuses for medical diagnostic imaging, non-destructive examinations, and the like using X-rays. Such radiographic imaging apparatuses are used, for example, in medical diagnostic imaging, as digital imaging apparatuses which capture still images as in general photography, moving images as in fluoroscopy, and the like.

One imaging method using FPDs is energy subtraction. In energy subtraction, a plurality of images corresponding to different energies are obtained by emitting X-rays at different tube voltages and the like, and the images are subjected to processing such as calculation to decompose bone images from soft tissue images, for example (PTL 1).

CITATION LIST

Patent Literature

PTL 1: Japanese Patent Laid-Open No. 2019-162358

When IVR (Interventional Radiology) is performed using an FPD, a contrast agent is injected into the blood vessels. In IVR, procedures are performed in which a catheter, guidewire, or the like is inserted into the blood vessel, and a stent, coil, or the like is then implanted. In IVR, the above-described procedures are performed while confirming the position and shape of contrast agents, medical devices, and the like by observing X-ray images obtained using an FPD, but the contrast of soft tissue, bone, and the like in the X-ray images can reduce visibility. Using energy subtraction to decompose images of soft tissue, bone, and the like from the X-ray images and removing the contrast thereof may improve the visibility of contrast agents, medical devices, and the like. However, there is a problem in that using energy subtraction to decompose soft tissue, bone, and the like increases noise.

SUMMARY OF THE INVENTION

The present invention provides a technique for reducing noise in an image obtained by energy subtraction processing.

According to one aspect of the present invention, there is provided an image processing apparatus comprising: a first processing unit configured to perform first noise reduction processing on a plurality of radiation images corresponding to mutually-different radiation energies; a generating unit configured to generate a decomposition image by energy subtraction processing using the plurality of radiation images obtained by performing the first noise reduction processing; and a second processing unit configured to perform second noise reduction processing on the decomposition image, the second noise reduction processing using a filter that differs from a filter used in the first noise reduction processing in at least one of size and type.

According to another aspect of the present invention, there is provided an image processing apparatus comprising: a generating unit that generates a decomposition image by energy subtraction processing using a plurality of radiation images corresponding to mutually-different radiation energies, and generates a pseudo decomposition image using a radiation image to which the energy subtraction processing is not applied and a predetermined constraint; and a determining unit that, using the decomposition image, determines a combining ratio pertaining to combining the decomposition image and the pseudo decomposition image.

According to another aspect of the present invention, there is provided an image processing method comprising: performing first noise reduction processing on a plurality of radiation images corresponding to mutually-different radiation energies; generating a decomposition image by energy subtraction processing using the plurality of radiation images obtained by performing the first noise reduction processing; and performing second noise reduction processing on the decomposition image, the second noise reduction processing using a filter that differs from a filter used in the first noise reduction processing in at least one of size and type.

According to another aspect of the present invention, there is provided an image processing method comprising: generating a decomposition image by energy subtraction processing using a plurality of radiation images corresponding to mutually-different radiation energies; generating a pseudo decomposition image using a radiation image to which the energy subtraction processing is not applied and a predetermined constraint; and determining, using the decomposition image, a combining ratio pertaining to combining of the decomposition image and the pseudo decomposition image.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4A is a diagram illustrating energy subtraction processing.

FIG. 9 is a diagram illustrating an example of a soft tissue image and a thickness image.

DESCRIPTION OF THE EMBODIMENTS

Figure 1:
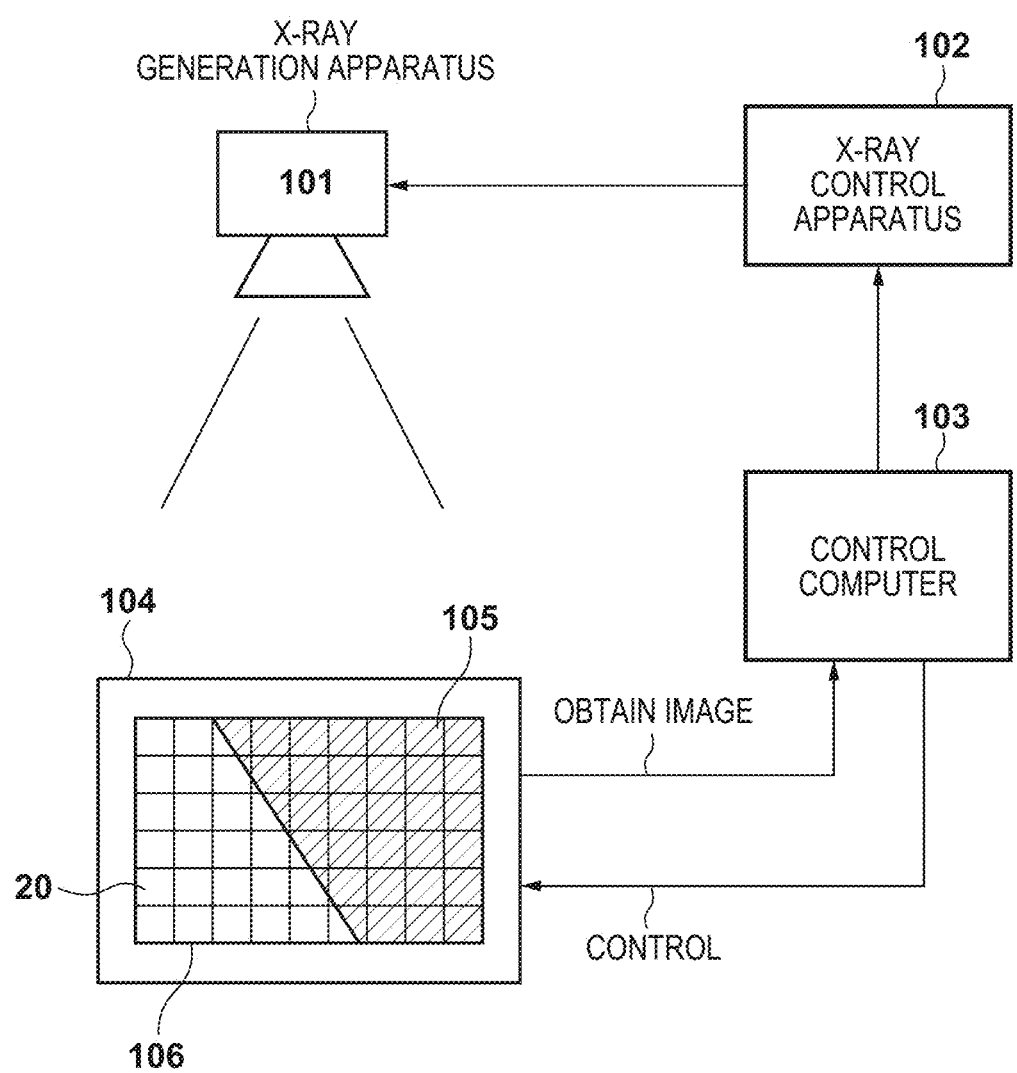
FIG. 1 is a diagram illustrating an example of the configuration of a radiation imaging system according to an embodiment.

Hereinafter, embodiments will be described in detail with reference to the attached drawings. Note, the following embodiments are not intended to limit the scope of the claimed invention, and limitation is not made to an invention that requires a combination of all features described in the embodiments. Two or more of the multiple features described in the embodiments may be combined as appropriate. Furthermore, the same reference numerals are given to the same or similar configurations, and redundant description thereof is omitted.

Although the following will describe a radiation imaging system that uses X-rays as radiation, the system is not limited thereto. In addition to α rays, β rays, γ rays, and the like, which are beams created by particles (including photons) emitted as a result of radiation decay, radiation according to the present invention is also assumed to include beams with the equivalent or higher energy, such as X-rays, particle beams, cosmic rays, and the like.

First Embodiment

FIG. 1 is a block diagram illustrating an example of the configuration of a radiation imaging system according to a first embodiment. The radiation imaging system of the first embodiment includes an X-ray generation apparatus 101, an X-ray control apparatus 102, a control computer 103, and an X-ray imaging apparatus 104.

The X-ray generation apparatus 101 emits X-rays. The X-ray control apparatus 102 controls the emission of X-rays by the X-ray generation apparatus 101. The control computer 103 controls the X-ray imaging apparatus 104 to obtain a radiation image (X-ray image (image information) hereinafter) captured by the X-ray imaging apparatus 104. The control computer 103 performs image processing, which will be described later, on the X-ray image obtained from the X-ray imaging apparatus 104. The X-ray imaging apparatus 104 is constituted by a phosphor 105 that converts radiation into visible light and a two-dimensional detector 106 that detects the visible light. The two-dimensional detector 106 is a sensor in which pixels 20 that detect X-ray quanta are disposed in an array of X columns×Y rows, and detects image information.

Figure 14:
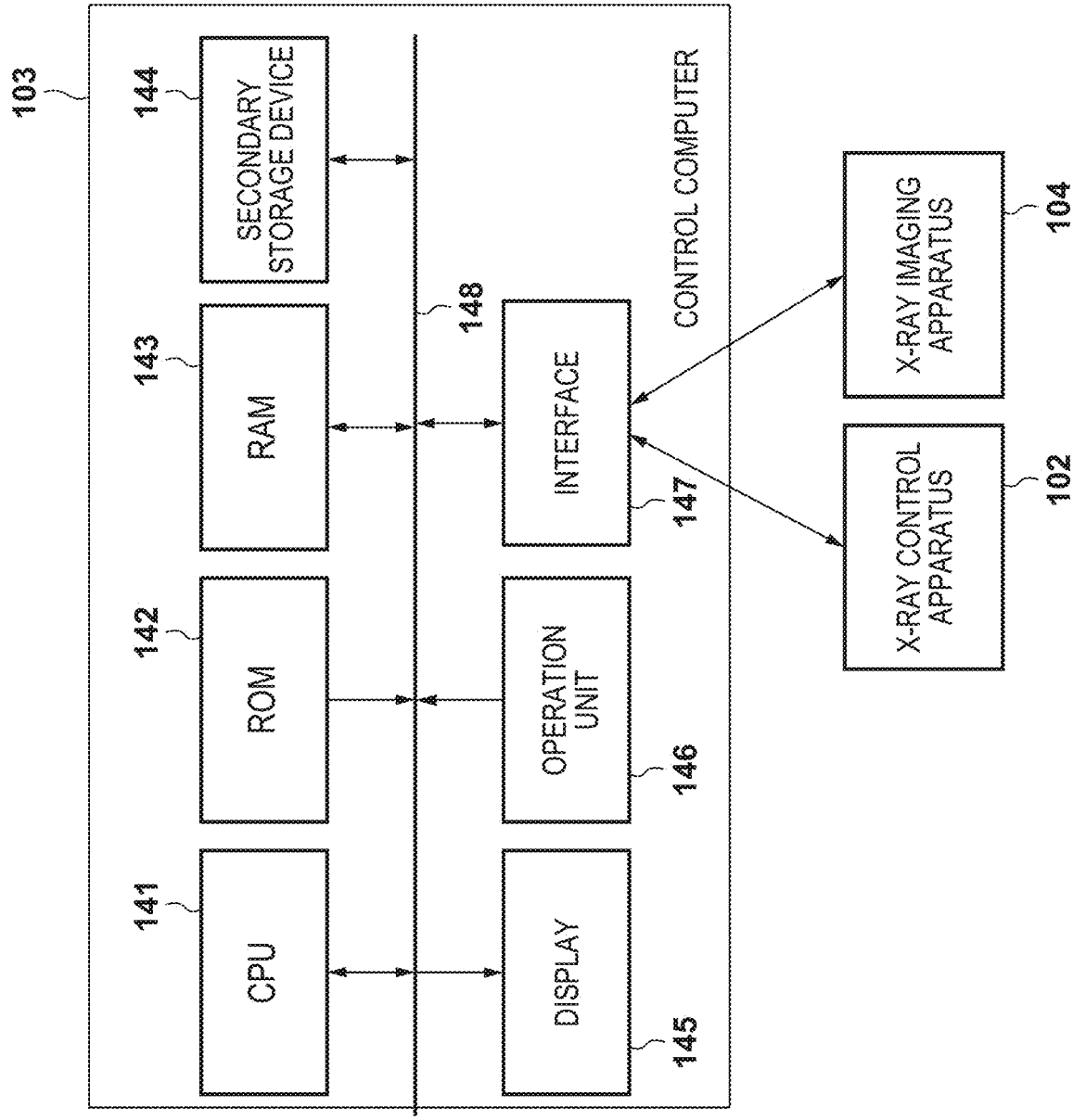
FIG. 14 is a block diagram illustrating an example of the hardware configuration of a control computer.

FIG. 14 is a block diagram illustrating an example of the hardware configuration of the control computer 103. A CPU 141 controls various operations of the control computer 103 by executing programs stored in ROM 142 or RAM 143. For example, the CPU 141 controls the X-ray irradiation by the X-ray control apparatus 102 (the X-ray generation apparatus 101) and the X-ray image capturing operation by the X-ray imaging apparatus 104. The CPU 141 also implements various types of signal processing and image processing, which will be described later. Some or all of the signal processing and image processing operations described later may be realized by dedicated hardware. The ROM 142 stores programs executed by the CPU 141, various types of data, and the like. The RAM 143 provides a work area for storing intermediate data and the like generated when the CPU 141 executes processing. A secondary storage device 144 stores the radiation image (X-ray image) to be processed. The secondary storage device 144 also stores control programs. The programs stored in the secondary storage device 144 are loaded into the RAM 143 as needed and executed by CPU 141.

A display 145 performs various displays under the control of the CPU 141. An operation unit 146 includes, for example, a keyboard and a pointing device, and accepts various inputs by a user. An interface 147 connects the control computer 103 with external devices such as the X-ray control apparatus 102, the X-ray imaging apparatus 104, and the like. A bus 148 communicatively connects the above-described units.

Figure 2:
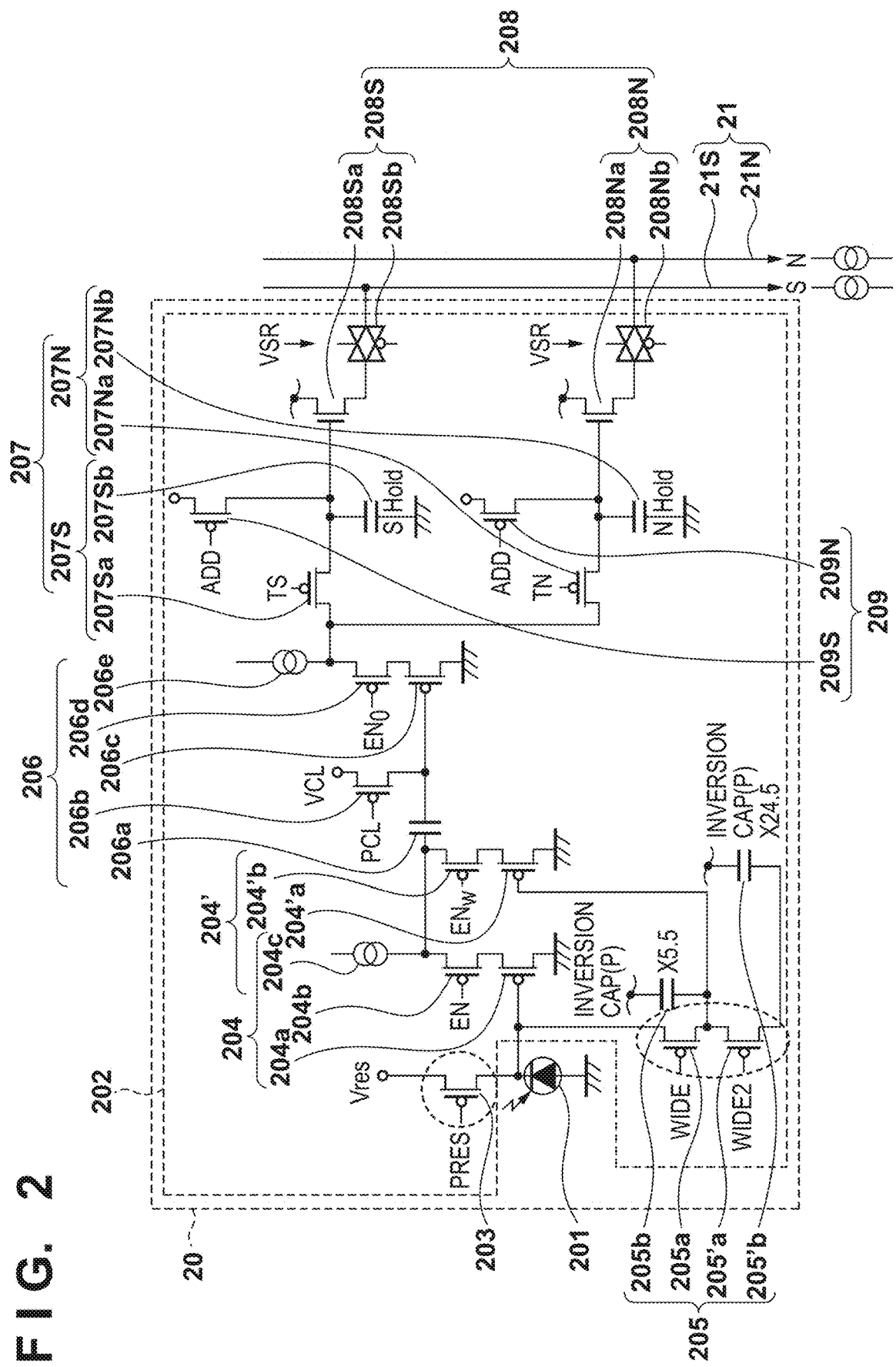
FIG. 2 is an equivalent circuit diagram of a pixel included in a two-dimensional detector of an X-ray imaging apparatus.

FIG. 2 is an equivalent circuit diagram of the pixel 20 included in the two-dimensional detector 106. The pixel 20 includes a photoelectric conversion element 201 and an output circuit unit 202. The photoelectric conversion element 201 can typically be a photodiode. The output circuit unit 202 includes an amplifier circuit unit 204, a clamp circuit unit 206, a sample hold circuit unit 207, and a selection circuit unit 208.

The photoelectric conversion element 201 includes a charge accumulating unit, and the charge accumulating unit is connected to a gate of a MOS transistor 204a of the amplifier circuit unit 204. A source of the MOS transistor 204a is connected to a current source 204c via a MOS transistor 204b. A source-follower circuit is constituted by the MOS transistor 204a and the current source 204c. The MOS transistor 204b is an enable switch that turns on when an enable signal EN supplied to the gate goes to an active level and puts the source-follower circuit into an operational state.

In the example illustrated in FIG. 2, the charge accumulating unit of the photoelectric conversion element 201 and the gate of the MOS transistor 204a constitute a common node, and this node functions as a charge-voltage conversion unit that converts the charge accumulated in the charge accumulating unit into a voltage. In other words, a voltage $V (=Q/C)$, which is determined by a charge Q accumulated in the charge accumulating unit and a capacitance value C of the charge-voltage conversion unit, arises in the charge-voltage conversion unit. The charge-voltage conversion unit is connected to a reset potential Vres via a reset switch 203. When a reset signal PRES goes to the active level, the reset switch 203 turns on, and a potential of the charge-voltage conversion unit is reset to the reset potential Vres.

The clamp circuit unit 206 uses a clamp capacitor 206a to clamp noise output by the amplifier circuit unit 204 according to the potential of the charge-voltage conversion unit which has been reset. In other words, the clamp circuit unit 206 is a circuit for canceling this noise from the signal output from the source-follower circuit in accordance with the charge generated through the photoelectric conversion performed by the photoelectric conversion element 201. This noise includes kTC noise at the time of the reset. Clamping is done by setting a clamp signal PCL to the active level and putting a MOS transistor 206b into an on state, and then setting the clamp signal PCL to an inactive level and putting the MOS transistor 206b into an off state. The output side of the clamp capacitor 206a is connected to a gate of a MOS transistor 206c. A source of the MOS transistor 206c is connected to a current source 206e via a MOS transistor 206d. A source-follower circuit is constituted by the MOS transistor 206c and the current source 206e. The MOS transistor 206d is an enable switch that turns on when an enable signal ENO supplied to the gate goes to an active level and puts the source-follower circuit into an operational state.

A signal output from the clamp circuit unit 206 in accordance with the charge produced through the photoelectric conversion by the photoelectric conversion element 201 is written, as an optical signal, to a capacitor 207Sb via a switch 207Sa when an optical signal sampling signal TS goes to the active level. The signal output from the clamp circuit unit 206 when the MOS transistor 206b has turned on immediately after the potential of the charge-voltage conversion unit has been reset is a clamp voltage. This noise signal is written into a capacitor 207Nb via a switch 207Na in response to a noise sampling signal TN going to the active level. This noise signal includes an offset component of the clamp circuit unit 206. A signal sample hold circuit 207S is constituted by the switch 207Sa and the capacitor 207Sb, and a noise sample hold circuit 207N is constituted by the switch 207Na and the capacitor 207Nb. The sample hold circuit unit 207 includes the signal sample hold circuit 207S and the noise sample hold circuit 207N.

When a drive circuit unit drives a row selection signal to the active level, the signal (optical signal) held in the capacitor 207Sb is output to a signal line 21S via a MOS transistor 208Sa and a row selection switch 208Sb. At the same time, the signal (noise) held in the capacitor 207Nb is output to a signal line 21N via a MOS transistor 208Na and a row selection switch 208Nb. Along with a constant current source (not shown) provided in the signal line 21S, the MOS transistor 208Sa constitutes a source-follower circuit. Likewise, along with a constant current source (not shown) provided in the signal line 21N, the MOS transistor 208Na constitutes a source-follower circuit. A signal selection circuit unit 208S is constituted by the MOS transistor 208Sa and the row selection switch 208Sb, and a noise selection circuit unit 208N is constituted by the MOS transistor 208Na and the row selection switch 208Nb. The selection circuit unit 208 includes the signal selection circuit unit 208S and the noise selection circuit unit 208N.

Each pixel 20 may include an adding switch 209S that adds the optical signals of a plurality of adjacent ones of the pixels 20. In an additive mode, an additive mode signal ADD goes to active level and the adding switch 209S turns on. This causes the capacitors 207Sb of the adjacent pixels 20 to be connected to each other by the adding switch 209S, which averages the optical signals. Likewise, each pixel 20 may include an adding switch 209N that adds the noise of a plurality of adjacent ones of the pixels 20. When the adding switch 209N turns on, the capacitors 207Nb of the adjacent pixels 20 are connected to each other by the adding switch 209N, which averages the noise. An adding unit 209 includes the adding switch 209S and the adding switch 209N.

The pixel 20 may include a sensitivity changing unit 205 for changing a sensitivity. The pixel 20 can include, for example, a first sensitivity changing switch 205a and a second sensitivity changing switch 205'a, along with circuit elements associated therewith. When a first changing signal WIDE goes to the active level, the first sensitivity changing switch 205a turns on, and a capacity value of the charge-voltage conversion unit is added to a capacity value of a first additional capacitor 205b. The sensitivity of the pixel 20 drops as a result. When a second changing signal WIDE2 goes to the active level, the second sensitivity changing switch 205'a turns on, and the capacity value of the charge-voltage conversion unit is added to a capacity value of a second additional capacitor 205'b. The sensitivity of the pixel 20 drops further as a result. By adding a function for reducing the sensitivity of the pixel 20 in this manner, a larger amount of light can be received and the dynamic range can be increased. When the first changing signal WIDE goes to the active level, an enable signal ENw may be set to the active level to cause a MOS transistor 204'a to function as a source-follower instead of the MOS transistor 204a.

The X-ray imaging apparatus 104 reads out the output of the pixel circuitry described above, converts the output to digital values using an AD converter, which is not shown, and then transfers an image to the control computer 103.

Figure 3A:
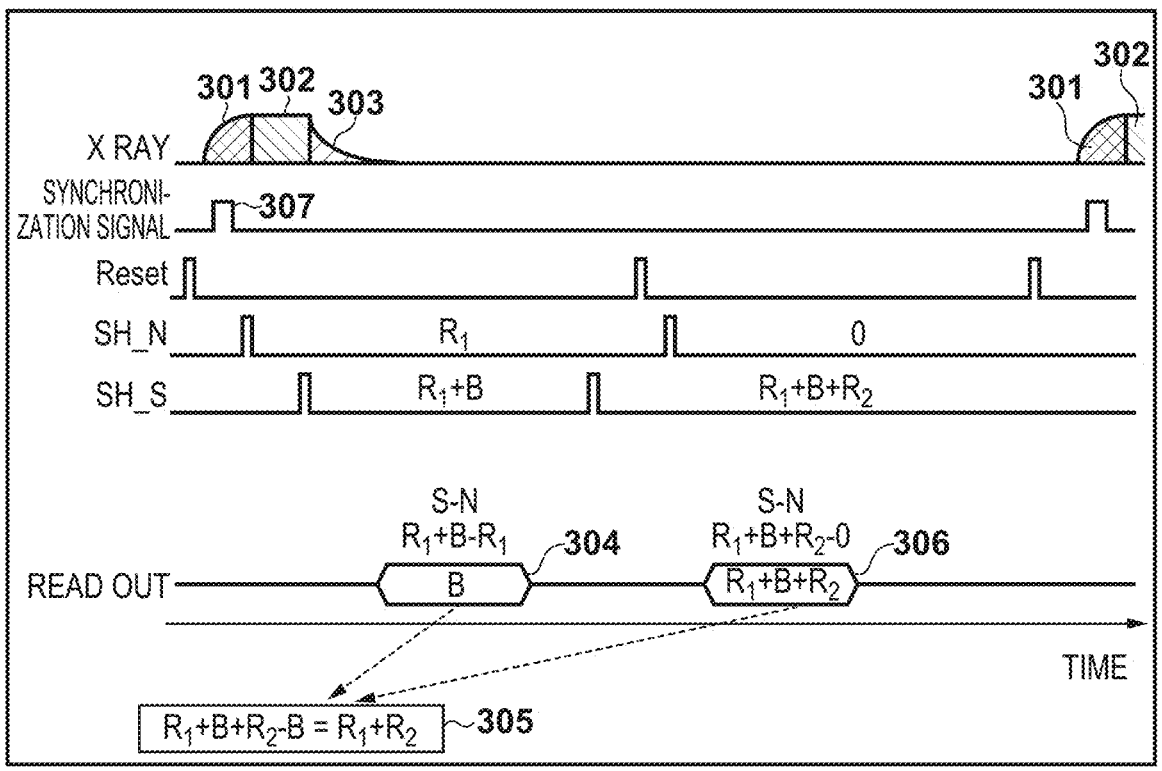
FIG. 3A is a timing chart illustrating operations for obtaining an X-ray image.
Figure 3B:
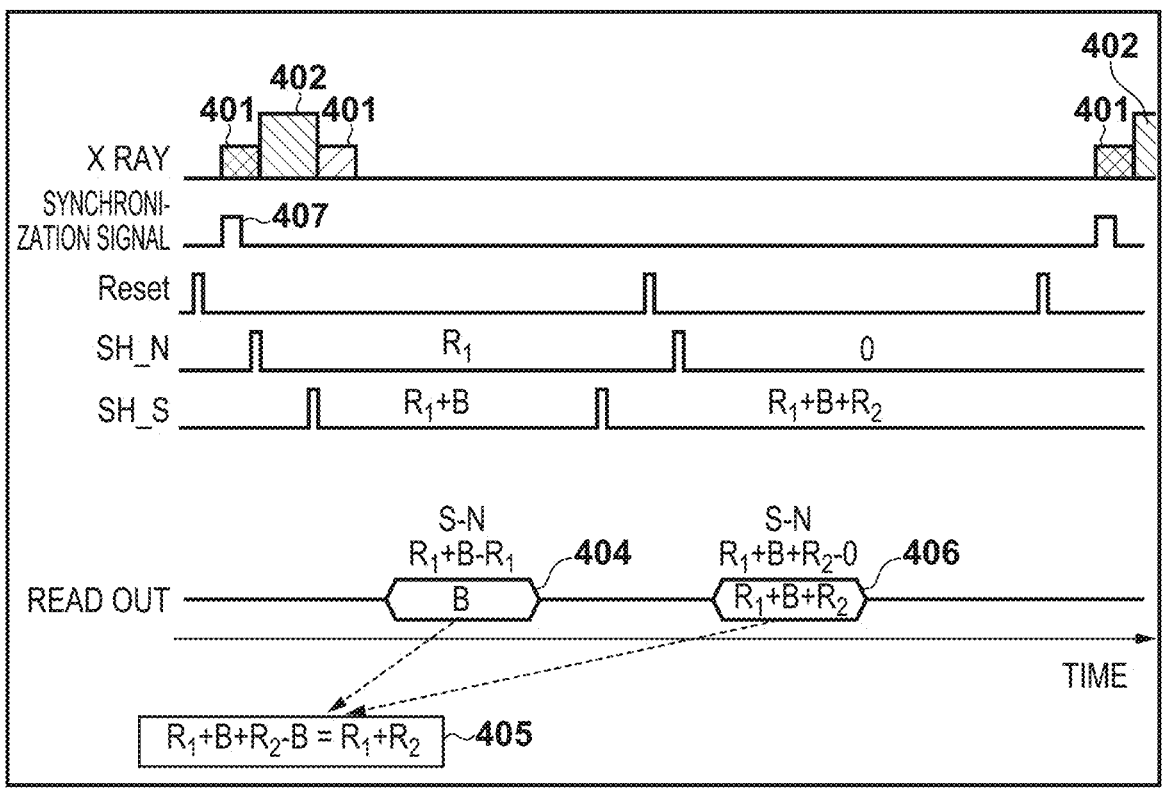
FIG. 3B is a timing chart illustrating operations for obtaining an X-ray image.

Operations of the radiation imaging system (driving of the X-ray imaging apparatus 104) according to the present embodiment will be described next. FIGS. 3A and 3B are diagrams illustrating the drive timing of the X-ray imaging apparatus 104 according to the first embodiment. In FIG. 3A, the horizontal axis represents time, indicating the timings of X-ray exposure, a synchronization signal, resetting of the photoelectric conversion element 201, the sample hold circuits 207, and image readout from signal lines 21.

First, the photoelectric conversion element 201 is reset before exposure to X-rays. The X-ray tube voltage is ideally a square wave, but the rise and fall of the tube voltage takes a finite amount of time. In particular, when the exposure time is short with pulsed X-rays, the tube voltage can no longer be considered a square wave, and the waveform is as illustrated in FIG. 3A. In other words, the X-ray energy differs among the rising phase, the stable phase, and the falling phase of the X-ray beam.

Therefore, sampling is performed by the noise sample hold circuit 207N after exposure by X-rays 301 in the rising phase, and sampling is then further performed by the signal sample hold circuit 207S after exposure by X-rays 302 in the stable phase. The difference between the signal line 21N and the signal line 21S is then read out as an image. At this time, the signal ($R_1$) of the X-rays 301 in the rising phase is held in the noise sample hold circuit 207N, and the sum ($R_1$+B) of the signal of the X-rays 301 in the rising phase and the signal of the X-rays 302 in the stable phase is held in the signal sample hold circuit 207S. Therefore, an image 304 corresponding to the signal (B) of the X-rays 302 in the stable phase is read out from the X-ray imaging apparatus 104.

Next, after the exposure by X-rays 303 in the falling phase and the readout of the image 304 are complete, sampling is again performed by the signal sample hold circuit 207S. The photoelectric conversion element 201 is then reset, sampled again by the noise sample hold circuit 207N, and the difference between the signal line 21N and the signal line 21S is read out as an image. At this time, the noise sample hold circuit 207N holds the signal in the state of no exposure by X-rays. The sum of the signal of the X-rays 301 in the rising phase, the X-rays 302 in the stable phase, and the X-rays 303 in the falling phase ($R_1+B+R_2$) is held in the signal sample hold circuit 207S. Therefore, an image 306 corresponding to the signal of the X-rays 301 in the rising phase, the signal of the X-rays 302 in the stable phase, and the signal of the X-rays 303 in the falling phase is read out from the X-ray imaging apparatus 104. Then, by calculating the difference between the image 306 and the image 304, an image 305, which corresponds to the sum of the X-rays 301 in the rising phase and the X-rays 303 in the falling phase ($R_1+R_2$), is obtained.

The timing for resetting the sample hold circuits 207 and the photoelectric conversion element 201 is determined using a synchronization signal 307, which indicates that X-ray exposure from the X-ray generation apparatus 101 has started. As a method for detecting the start of X-ray exposure, for example, a configuration that measures the tube current of the X-ray generation apparatus 101 and determines whether the current value exceeds a pre-set threshold can be used. Alternatively, for example, a configuration may be used in which the pixels 20 are repeatedly read out after the resetting of the photoelectric conversion element 201 is completed, and it is determined whether the pixel value exceeds a pre-set threshold. Alternatively, for example, a configuration may be used in which the X-ray imaging apparatus 104 incorporates an X-ray detector different from the two-dimensional detector 106, and it is determined whether a value measured thereby exceeds a pre-set threshold. Regardless of the configuration, the sampling of the signal sample hold circuit 207S, the sampling of the noise sample hold circuit 207N, and the resetting of the photoelectric conversion element 201 are performed after a predetermined amount of time has elapsed following the input of the synchronization signal 307.

In this manner, the image 304 corresponding to the stable phase of the pulsed X-rays and the image 305 corresponding to the sum of the rising phase and the falling phase are obtained. Because the X-ray energies emitted when forming the two images are different, energy subtraction processing can be performed by performing computations between the images.

FIG. 3B illustrates a drive timing when energy subtraction is performed in the radiation imaging system according to the first embodiment. This differs from FIG. 3A in that the X-ray tube voltage is actively switched.

First, the photoelectric conversion element 201 is reset before exposure to low-energy X-rays 401. Then, after sampling by the noise sample hold circuit 207N, the tube voltage is switched and exposure is performed with high-energy X-rays 402, and sampling is performed by the signal sample hold circuit 207S. The tube voltage is then switched, and exposure is performed with low-energy X-rays 403. Furthermore, the difference between the signal line 21N and the signal line 21S is read out as an image. At this time, the signal of the low-energy X-rays 401 ($R_1$) is held in the noise sample hold circuit 207N, and the sum of the signals of the low-energy X-rays 401 and the high-energy X-rays 402 ($R_1+B$) is held in the signal sample hold circuit 207S. Therefore, an image 404 corresponding to the signal (B) of the high-energy X-rays 402 is read out from the X-ray imaging apparatus 104.

Next, after the exposure by the low-energy X-rays 403 and the readout of the image 404 are complete, sampling is again performed by the signal sample hold circuit 207S. The photoelectric conversion element 201 is then reset, sampled again by the noise sample hold circuit 207N, and the difference between the signal line 21N and the signal line 21S is read out as an image. At this time, the noise sample hold circuit 207N holds a signal from a state of no X-ray exposure, and the signal sample hold circuit 207S holds the sum of the signal of the low-energy X-rays 401, the high-energy X-rays 402, and the low-energy X-rays 403 ($R_1+B+R_2$). Accordingly, an image 406 corresponding to the signal of the low-energy X-rays 401, the signal of the high-energy X-rays 402, and the signal of the low-energy X-rays 403 is read out from the X-ray imaging apparatus 104. The difference between the image 406 and the image 404 is then calculated, and an image 405, which corresponds to the sum ($R_1+R_2$) of the low-energy X-rays 401 and the low-energy X-rays 403, is obtained. A synchronization signal 407 is similar to that in FIG. 3A. In this manner, by obtaining images while actively switching the tube voltage, the energy difference between the low-energy and high-energy images can be made greater than when using the method illustrated in FIG. 3A.

Next, the energy subtraction processing of the present embodiment will be described with reference to FIGS. 4A to 4C. The energy subtraction processing in the present embodiment is divided into three stages, namely correction processing, signal processing, and image processing. The following will describe the processing in each stage.

Description of Correction Processing

FIG. 4A illustrates a block diagram of the correction processing in the energy subtraction processing according to the present embodiment. First, imaging is performed without X-ray exposure to the X-ray imaging apparatus 104, and images are obtained using the driving illustrated in FIG. 3A or FIG. 3B. Two images are read out at this time, with the first image being F_ODD and the second image being F_EVEN. F_ODD and F_EVEN are images corresponding to fixed pattern noise (FPN) of the X-ray imaging apparatus 104. Next, imaging is performed with X-ray exposure to the X-ray imaging apparatus 104 in a state where there is no subject, and images are obtained using the driving illustrated in FIG. 3A or FIG. 3B. Two images are read out at this time, with the first image being W_ODD and the second image being W_EVEN. W_ODD and W_EVEN are images corresponding to the sum of the FPN of the X-ray imaging apparatus 104 and the signal produced by the X-rays. Therefore, by subtracting F_ODD from W_ODD and F_EVEN from W_EVEN, images WF_ODD and WF_EVEN, from which the FPN of the X-ray imaging apparatus 104 is removed, are obtained. This is called "offset correction".

WF_ODD is an image corresponding to the X-rays 302 in the stable phase (or the high-energy X-rays 402). WF_EVEN is the image corresponding to the sum of the X-rays 301 in the rising phase, the X-rays 302 in the stable phase, and the X-rays 303 in the falling phase (or the sum of the low-energy X-rays 401 and 403 and the high-energy X-rays 402). Therefore, by subtracting WF_ODD from WF_EVEN, an image corresponding to the sum of the X-rays 301 in the rising phase and the X-rays 303 in the falling phase is obtained. The energy of the X-rays 301 in the rising phase and the X-rays 303 in the falling phase is lower than the energy of the X-rays 302 in the stable phase. Therefore, by subtracting WF_ODD from WF_EVEN, a low-energy image W_Low when there is no subject is obtained. A high-energy image W_High when there is no subject is obtained from WF_ODD. This is called "color correction".

Next, imaging is performed with X-ray exposure to the X-ray imaging apparatus 104 in a state where there is a subject, and images are obtained using the driving illustrated in FIG. 3A or FIG. 3B. Two images are read out at this time, with the first image being X_ODD and the second image being X_EVEN. By performing similar subtraction as in the case where there is no subject, a low-energy image X_Low for the case where there is a subject and a high-energy image X_High for the case where there is a subject are obtained.

Here, assuming the thickness of the subject is d, the linear attenuation coefficient of the subject is µ, the output of the pixel 20 when there is no subject is $I_0$, and the output of the pixel 20 when there is a subject is I, the following Formula (1) is established.

[Math 1]

$$I=I_0 \exp(-\mu d) \quad (1)$$

Transforming Formula (1) results in the following Formula (2). The right side of Formula (2) indicates the attenuation rate of the subject. The attenuation rate of the subject is a real number between 0 and 1.

[Math 2]

$$I/I_0 = \exp(-\mu d) \quad (2)$$

Therefore, by dividing the low-energy image X_Low for the case where there is a subject by the low-energy image W_Low for the case where there is no subject, an image L of the attenuation rate at low energy is obtained. Likewise, by dividing the high-energy image X_High for the case where there is a subject by the high-energy image W_High for the case where there is no subject, an image H of the attenuation rate at high energy is obtained. This is called "gain correction".

Description of Signal Processing

Figure 4B:
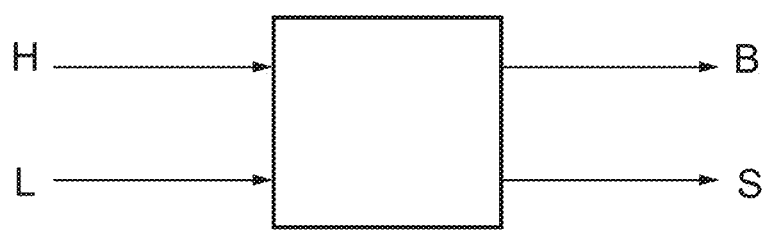
FIG. 4B is a diagram illustrating energy subtraction processing.

FIG. 4B illustrates a block diagram of the signal processing in the energy subtraction processing. In signal processing, decomposition images are obtained from the image L of the attenuation rate at low energy and the image H of the attenuation rate at high energy, which have been obtained by the correction processing illustrated in FIG. 4A. Here, a case where an image B of a bone thickness (also called a "bone image B") and an image S of a soft tissue thickness (also called a "soft tissue image S") are obtained will be described as an example of the decomposition images.

First, if the energy of X-ray photons is E, the number of photons at energy E is N(E), the thickness of bone is B, the thickness of soft tissue is S, the linear attenuation coefficient of bone at energy E is $\mu_B(E)$, the linear attenuation coefficient of soft tissue at energy E is $\mu_S(E)$, and the attenuation rate is $I/I_0$, the following Formula (3) is established.

[Math 3]

$$I/I_0 = \frac{\int_0^\infty N(E)\exp\{-\mu_B(E)B - \mu_S(E)S\}EdE}{\int_0^\infty N(E)EdE} \quad (3)$$

The number of photons N(E) at energy E is the X-ray spectrum. X-ray spectrum is obtained through simulations or actual measurement. The linear attenuation coefficient $\mu_B(E)$ of bone at energy E and the linear attenuation coefficient $\mu_S(E)$ of soft tissue at energy E can be obtained from databases such as NIST. In other words, it is possible to calculate the attenuation rate $I/I_0$ at any given bone thickness B, soft tissue thickness S, and X-ray spectrum N(E).

Here, if the spectrum in low-energy X-rays is $N_L(E)$ and the spectrum in high-energy X-rays is $N_H(E)$, the following Formula (4) is established.

[Math 4]

$$L = \frac{\int_0^\infty N_L(E)\exp\{-\mu_B(E)B - \mu_S(E)S\}EdE}{\int_0^\infty N_L(E)EdE} \quad (4)$$

$$H = \frac{\int_0^\infty N_H(E)\exp\{-\mu_B(E)B - \mu_S(E)S\}EdE}{\int_0^\infty N_H(E)EdE}$$

By solving the nonlinear simultaneous equations in Formula (4), the bone thickness B and soft tissue thickness S can be obtained. The Newton-Raphson method will be described as a typical method for solving nonlinear simultaneous equations. First, if the number of iterations of the Newton-Raphson method is m, the bone thickness after the mth iteration is $B^m$, and the soft tissue thickness after the mth iteration is $S^m$, the following Formula (5) expresses the high-energy attenuation rate after the mth iteration as $H^m$ and the low-energy attenuation rate after the mth iteration as $L^m$.

[Math 5]

$$L^m = \frac{\int_0^\infty N_L(E)\exp\{-\mu_B(E)B^m - \mu_S(E)S^m\}EdE}{\int_0^\infty N_L(E)EdE} \quad (5)$$

$$H^m = \frac{\int_0^\infty N_H(E)\exp\{-\mu_B(E)B^m - \mu_S(E)S^m\}EdE}{\int_0^\infty N_H(E)EdE}$$

The rate of change of the attenuation rate for minute changes in thickness is expressed by the following Formula (6).

[Math 6]

$$\frac{\partial H^m}{\partial B^m} = \frac{\int_0^\infty -\mu_B(E)N_H(E)\exp\{-\mu_B(E)B^m - \mu_S(E)S^m\}EdE}{\int_0^\infty N_H(E)EdE} \quad (6)$$

$$\frac{\partial L^m}{\partial B^m} = \frac{\int_0^\infty -\mu_B(E)N_L(E)\exp\{-\mu_B(E)B^m - \mu_S(E)S^m\}EdE}{\int_0^\infty N_L(E)EdE}$$

$$\frac{\partial H^m}{\partial S^m} = \frac{\int_0^\infty -\mu_S(E)N_H(E)\exp\{-\mu_B(E)B^m - \mu_S(E)S^m\}EdE}{\int_0^\infty N_H(E)EdE}$$

-continued $$\frac{\partial L^m}{\partial S^m} = \frac{\int_0^\infty -\mu_S(E)N_L(E)\exp\{-\mu_B(E)B^m - \mu_S(E)S^m\}EdE}{\int_0^\infty N_L(E)EdE}$$

A bone thickness $B^{m+1}$ and a soft tissue thickness $S^{m+1}$ after the m+1th iteration are expressed by the following Formula (7), using the high-energy attenuation rate H and the low-energy attenuation rate L.

[Math 7]

$$\begin{bmatrix} B^{m+1} \\ S^{m+1} \end{bmatrix} = \begin{bmatrix} B^m \\ S^m \end{bmatrix} + \begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} \begin{bmatrix} H - H^m \\ L - L^m \end{bmatrix} \quad (7)$$

Assuming the determinant is det, the inverse of the 2×2 matrix is represented by the following Formula (8), based on Cramer's rule.

[Math 8]

$$\det = \frac{\partial H^m}{\partial B^m}\frac{\partial L^m}{\partial S^m} - \frac{\partial H^m}{\partial S^m}\frac{\partial L^m}{\partial B^m} \begin{bmatrix} \frac{\partial H^m}{\partial B^m} & \frac{\partial H^m}{\partial S^m} \\ \frac{\partial L^m}{\partial B^m} & \frac{\partial L^m}{\partial S^m} \end{bmatrix}^{-1} \quad (8)$$

$$= \frac{1}{\det}\begin{bmatrix} \frac{\partial L^m}{\partial S^m} & -\frac{\partial H^m}{\partial S^m} \\ -\frac{\partial L^m}{\partial B^m} & \frac{\partial H^m}{\partial B^m} \end{bmatrix}$$

Therefore, substituting Formula (8) into Formula (7) results in the following Formula (9).

[Math 9]

$$B^{m+1} = B^m + \frac{1}{\det}\frac{\partial L^m}{\partial S^m}(H - H^m) - \frac{1}{\det}\frac{\partial H^m}{\partial S^m}(L - L^m) \quad (9)$$

$$S^{m+1} = S^m - \frac{1}{\det}\frac{\partial L^m}{\partial B^m}(H - H^m) + \frac{1}{\det}\frac{\partial H^m}{\partial B^m}(L - L^m)$$

By repeating these calculations, the difference between the high-energy attenuation rate $H^m$ after the mth iteration and the measured high-energy attenuation rate H continues to approach zero without limit. The same is true for the low-energy attenuation rate L. As a result, the bone thickness $B^m$ after the mth iteration converges on the bone thickness B, and the soft tissue thickness $S^m$ after the mth iteration converges on the soft tissue thickness S. In this manner, the nonlinear simultaneous equations indicated in Formula (4) can be solved. Therefore, by calculating Formula (4) for all pixels, the image B of the bone thickness and the image S of the soft tissue thickness can be obtained from the image L of the attenuation rate at low energy and the image H of the attenuation rate at high energy.

Although an example in which images of the bone thickness B and the soft tissue thickness S are calculated has been described as an example of the decomposition images in the present embodiment, the present embodiment is not limited to this form. For example, the thickness W of water and the thickness I of a contrast agent may be calculated as the decomposition images. In other words, the image may be broken down into the thicknesses of any two types of materials. An image of an effective atomic number Z and an image of an areal density D may be obtained as the decomposition images from the image L of the attenuation rate at low energy and the image H of the attenuation rate at high energy obtained through the correction processing illustrated in FIG. 4A. The effective atomic number Z is the equivalent atomic number of a mixture, and the areal density D is the product of the density of the subject [g/cm$^3$] and the thickness of the subject [cm]. Naturally, the decomposition images may be generated by performing other operations on the low energy image and the high energy image. In other words, it can be said that the signal processing of the present invention is processing of generating an energy subtraction image by computing a low energy image and a high energy image (energy subtraction processing). In the present specification, "energy subtraction image" and "decomposition image" are assumed to be synonymous.

Additionally, although the present embodiment describes an example of solving nonlinear simultaneous equations using the Newton-Raphson method, the embodiment is not limited thereto. For example, an iterative solution method such as the least-squares method or the bisection method may be used. Additionally, although the nonlinear simultaneous equations are solved by an iterative solution method in the present embodiment, the embodiment is not limited thereto. A table may be generated by obtaining the bone thickness B and soft tissue thickness S for various combinations of the high-energy attenuation rate H and the low-energy attenuation rate L in advance, and a configuration for obtaining the bone thickness B and soft tissue thickness S quickly by referring to this table may be used.

Description of Image Processing for Display

Figure 4C:
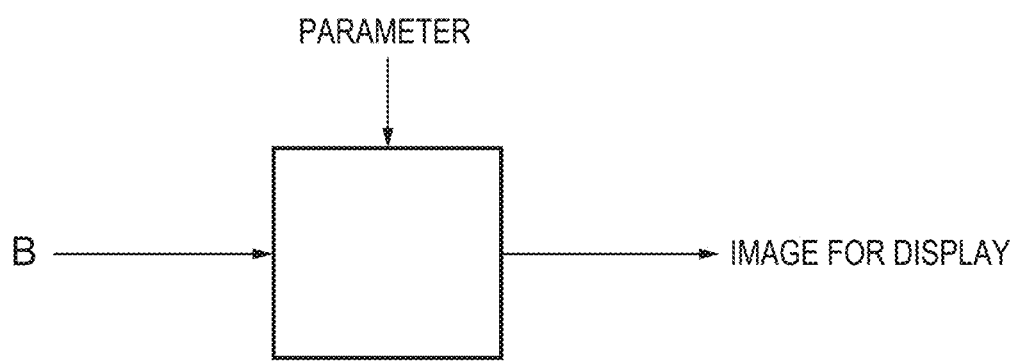
FIG. 4C is a diagram illustrating energy subtraction processing.

FIG. 4C illustrates a block diagram of image processing for display in the energy subtraction processing. In the image processing for display, an image for display is generated using the decomposition images obtained through the above-described signal processing. For example, the image for display is generated by performing post-processing on the bone image B obtained through the signal processing illustrated in FIG. 4B. The generated image for display is displayed, for example, in the display 145. Logarithmic transformation, dynamic range compression, and the like can be used as the post-processing. The details of the processing may be switched by inputting the type, strength, and the like of the post-processing as parameters.

Figure 5:
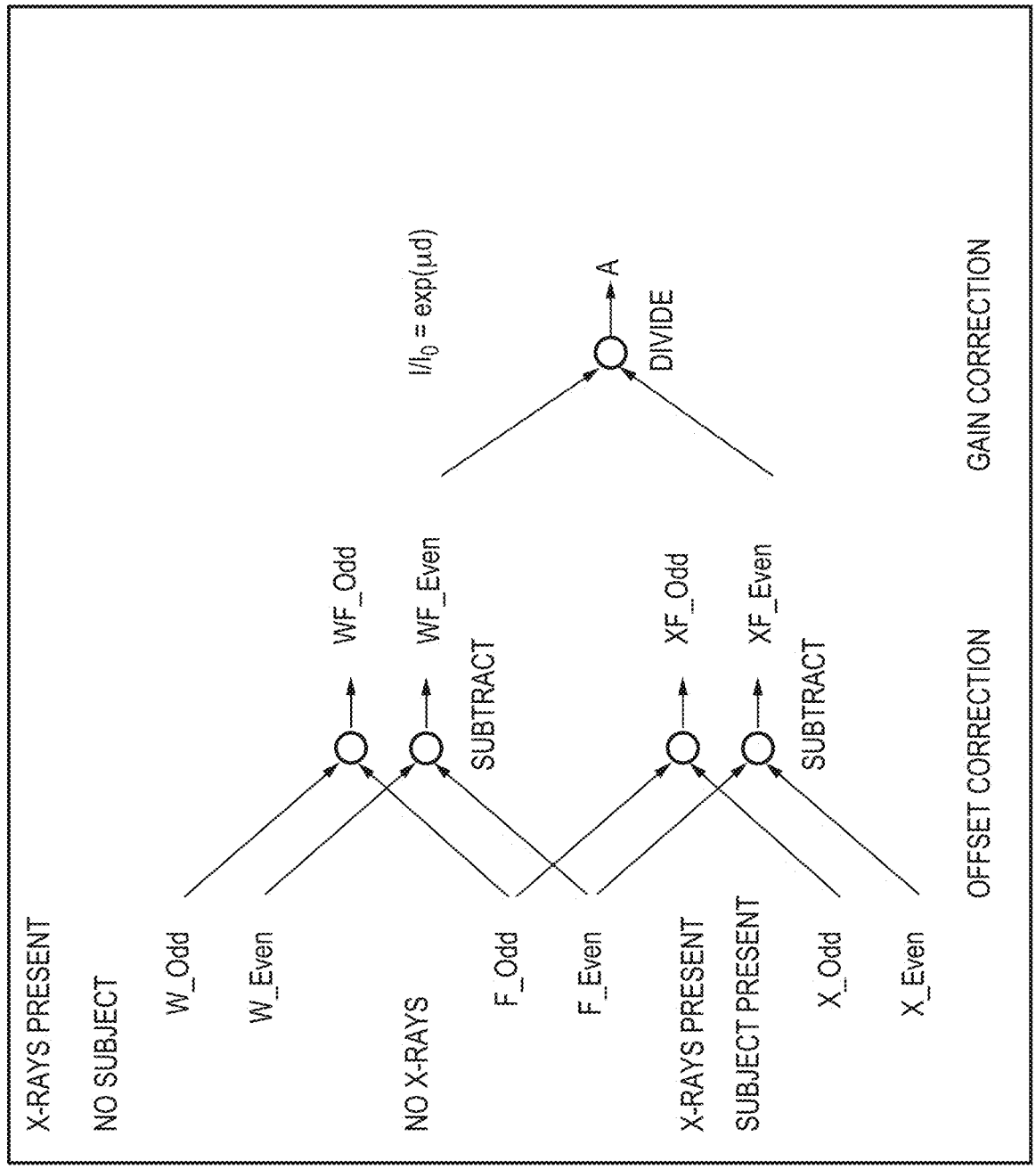
FIG. 5 is a diagram illustrating processing of obtaining an accumulation image A.

The foregoing has been a description of the energy subtraction processing. The signal processing and the image processing for display in the energy subtraction processing will be collectively referred to as "image processing" hereinafter. The following embodiment describes a configuration that effectively reduces noise using accumulation images in the image processing described above. First, the accumulation image used in the present embodiment will be described. As mentioned above, in the present embodiment, for a single instance of X-ray irradiation, a high-energy image and a low-energy image are generated from a plurality of radiation images obtained by sampling and holding at a plurality of timings, including during and after X-ray irradiation. For example, an X-ray image obtained at a timing after the end of X-ray irradiation can be used as the accumulation image. FIG. 5 is a block diagram illustrating an example of a configuration that realizes the correction processing for obtaining an accumulation image according to the present embodiment. The accumulation image A, which is an image that does not have energy resolution, i.e., an image compatible with images captured using existing radiation imaging systems, can be used as the image for display in the display 145. As illustrated in FIG. 5, for example, the accumulation image A is generated by dividing the image XF_EVEN by the image WF_EVEN. The image XF_EVEN and the image WF_EVEN are as described with reference to FIG. 4A. In other words, the image XF_EVEN corresponds to the sum of the X-rays 301 in the rising phase, the X-rays 302 in the stable phase, and the X-rays 303 in the falling phase when there is a subject. The image WF_EVEN corresponds to the sum of the X-rays 301 in the rising phase, the X-rays 302 in the stable phase, and the X-rays 303 in the falling phase when there is no subject.

Note that the accumulation image A may be generated by adding the image H of the attenuation rate at high energy and the image L of the attenuation rate at low energy, multiplied by coefficients. For example, the accumulation image A can be generated using Formula (10). Note that in the calculation of the accumulation image A, one coefficient may be set to 0 and the other to 1, and the image H or the image L itself can be used as the accumulation image A. In other words, an image for which the timing of the capture is substantially the same as that of the image subject to energy subtraction processing, but to which the energy subtraction processing has not been applied, can be used as the accumulation image A.

[Math 10]
$$A = XF\_EVEN/WF\_EVEN \quad (10)$$
$$= X\_High/WF\_EVEN + X\_Low/WF\_EVEN$$
$$= H*(W\_High/WF\_EVEN) + L*(W\_Low/WF\_EVEN)$$

Figure 6:
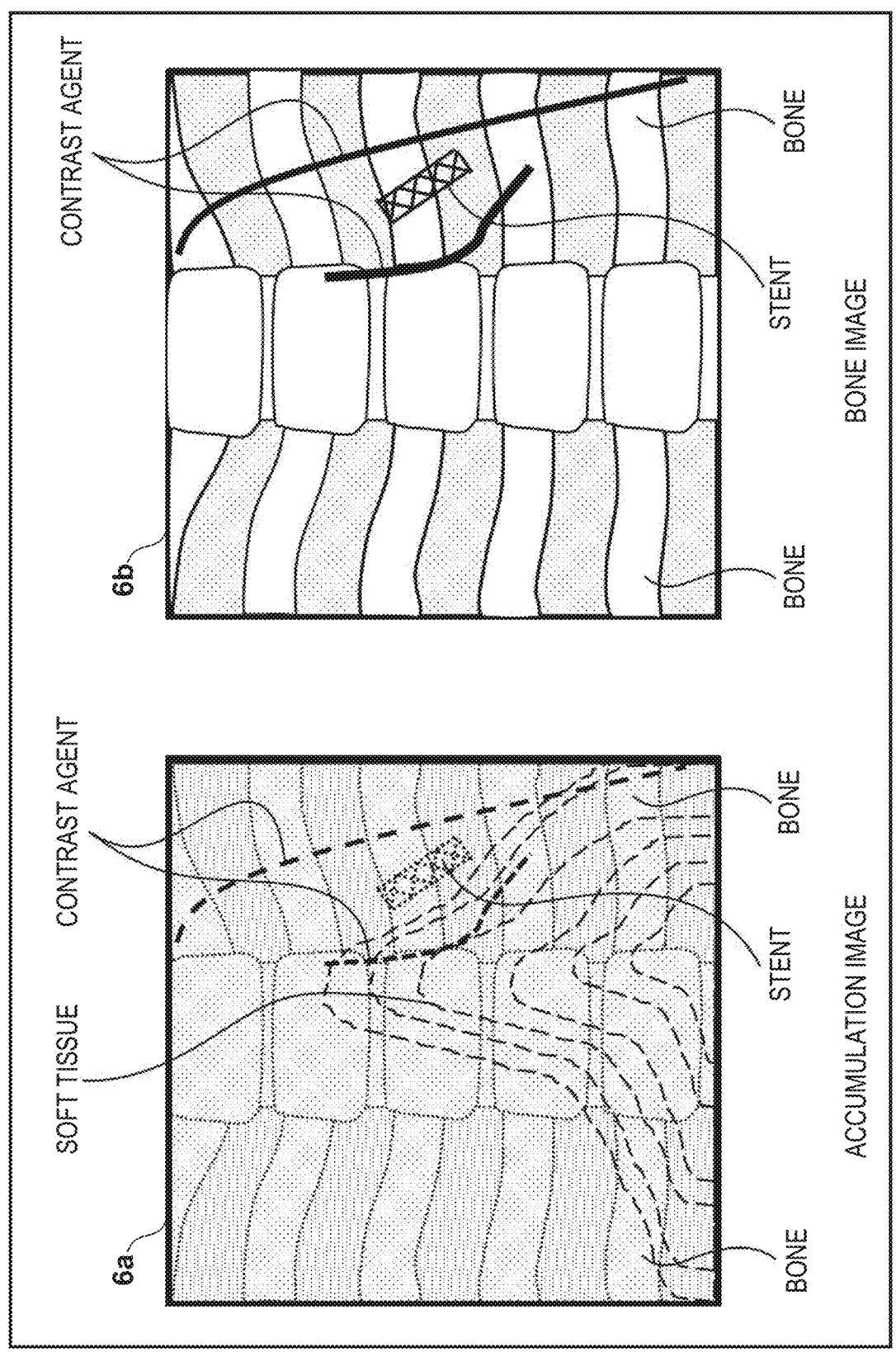
FIG. 6 is a diagram illustrating an example of an accumulation image and a bone image.

FIG. 6 illustrates examples of the accumulation image A and the bone image B. The normal human body consists only of soft tissue and bone. When IVR (Interventional Radiology) is performed using the radiation imaging system illustrated in FIG. 1, a contrast agent is injected into the blood vessels. Additionally, procedures are performed in which a catheter, guidewire, or the like is inserted into the blood vessel, and a stent, coil, or the like is then implanted. In IVR, the procedures are performed while checking the position and shape of contrast agents, medical devices, and the like. Accordingly, it is desirable to improve visibility by using energy subtraction processing to decompose images of only contrast agents or medical devices, or by removing background (images) such as soft tissue or bone.

An accumulation image 6a in FIG. 6 is an example of the accumulation image A described above. As illustrated in FIG. 6, soft tissue is visible in an image compatible with normal radiation imaging systems, i.e., the accumulation image A. On the other hand, a bone image 6b in FIG. 6 is an example of the bone image B described above. As illustrated in FIG. 6, the contrast of soft tissue can be removed in the bone image B in the radiation imaging system according to the present embodiment. The primary component of a contrast agent media is iodine, and the primary component of medical devices is metal such as stainless steel. Both have a higher atomic number than calcium, which is the primary component of bone, and thus bone, contrast agents, and medical devices are displayed in the bone image B. Upon carrying out investigations, the inventors of the present application confirmed that bone, contrast agents, and medical devices are displayed in the contrast agent image I, even if the high-energy image H and the low-energy image L are decomposed into the water image W and the contrast agent image I, for example. The same is true for any other combination of two materials. Additionally, the same is true when the tube voltages, filters, and the like for low-energy X-rays and high-energy X-rays are changed. In any case, the bone image B was confirmed to show bone, contrast agents, and medical devices.

In cases where soft tissue contrast reduces visibility, such as in lung field areas when performing IVR of the chest, the visibility of the contrast agent or medical device may be improved by displaying the bone image B in the radiation imaging system according to the present embodiment. However, there is a problem in that the bone image B has more noise than the accumulation image A, which reduces the image quality. Therefore, noise reduction of the bone image B is performed in the present embodiment. For noise reduction, a configuration in which noise reduction processing is performed on the image after decomposition through energy subtraction processing, and a configuration in which noise reduction processing is performed on the image before decomposition through energy subtraction processing, can be considered.

Figure 7A:
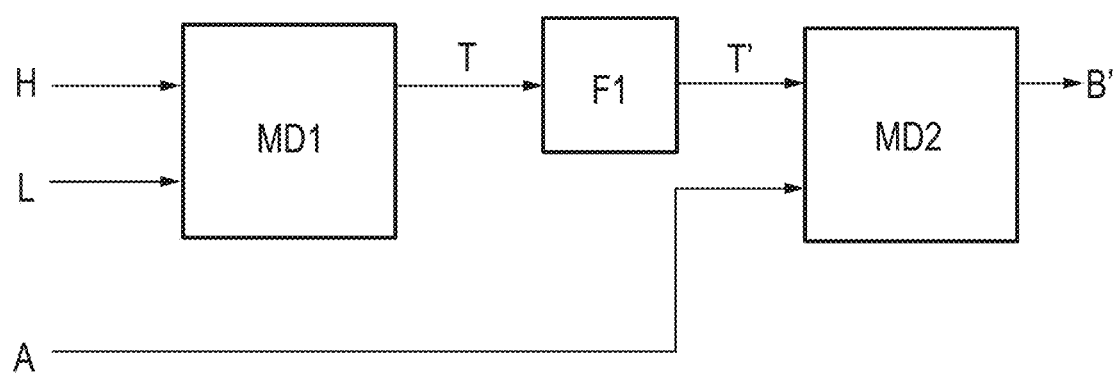
FIG. 7A is a block diagram illustrating image processing involved in noise reduction processing.

FIG. 7A illustrates a block diagram of image processing that performs noise reduction processing on the image after decomposition through energy subtraction processing. First, in block MD1, the bone image B and the soft tissue image S are obtained from the low-energy image L and the high-energy image H through a procedure similar to the image processing in FIG. 4B, and then a thickness image T is generated by adding the bone image B and the soft tissue image S. Then, in block F1, filter processing is applied to the thickness image T for the purpose of noise reduction, and a filtered thickness image T' is generated. For example, a spatial filter such as Gaussian and median filters, a structure-preserving spatial filter such as epsilon and Laplacian filters, and a temporal filter such as a recursive filter can be used to filter block F1.

Next, in block MD2, a noise-reduced bone image B' is generated from the filtered thickness image T' and the accumulation image A described above. Under the assumption (constraint condition) that the accumulation image A consists only of bone and soft tissue, if the spectrum in the accumulation image A is $N_A(E)$, the thickness of soft tissue is S, and the thickness of bone is B, the following Formula (11) is established.

[Math 11]
$$A = \frac{\int N_A(E)\exp\{-\mu_B(E)B - \mu_S(E)S\}EdE}{\int N_A(E)EdE} \quad (11)$$

If T is the sum of the bone thickness and soft tissue thickness, based on T=B+S, the following Formula (12) is obtained by transforming Formula (11).

[Math 12]
$$A = \frac{\int N_A(E)\exp\{-\mu_B(E)B - \mu_S(E)(T - B)\}EdE}{\int N_A(E)EdE} \quad (12)$$

By substituting the pixel value A and thickness T of the accumulation image at a given pixel in Formula (12) and solving the nonlinear equation, the bone thickness B at a given pixel can be obtained. At this time, if the filtered thickness T' is substituted in place of the thickness T and Formula (12) is solved, the bone thickness B' is obtained. The thickness image T has a higher continuity than the accumulation image A and therefore does not contain high-frequency components. Therefore, signal components are unlikely to be lost even if noise is removed through filter processing. By using the noise-reduced thickness image T' and the originally low-noise accumulation image A, the noise-reduced bone image B' can be obtained. Similarly, it is also possible to obtain a noise-reduced soft tissue image S' by transforming Formula (11) using B=T−S. Furthermore, although a combined image T is used here, the image is not limited thereto. For example, the noise-reduced bone image B' may be obtained by substituting the pixel values of the noise-reduced soft tissue image S', which is obtained by performing noise reduction on the soft tissue image S generated in MD1 using block F1, into Formula (11). Likewise, the noise-reduced soft tissue image S' may be obtained by substituting the pixel values of the noise-reduced bone image B', which is obtained by performing noise reduction on the bone image B generated in MD1 using block F1, into Formula (11).

Figure 7B:
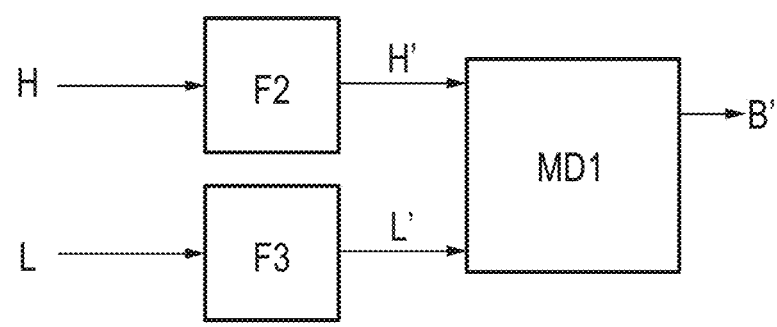
FIG. 7B is a block diagram illustrating image processing involved in noise reduction processing.

A configuration for image processing that performs noise reduction processing on the image before decomposition through energy subtraction processing will be described next. FIG. 7B illustrates a block diagram of the image processing that performs noise reduction processing on the image before decomposition. Blocks F2 and F3 apply filter processing for the purpose of noise reduction to the low-energy image L and the high-energy image H, respectively, and a noise-reduced low-energy image L' and a noise-reduced high-energy image H' are generated as a result. For example, a spatial filter such as Gaussian and median filters, a structure-preserving spatial filter such as epsilon and Laplacian filters, and a temporal filter such as a recursive filter can be used for the filter processing. In block MD1, a noise-reduced bone image B' is obtained from the noise-reduced low-energy image L' and the noise-reduced high-energy image H', using a procedure similar to that in FIG. 4B.

In noise reduction processing where a filter is applied after block MD1, where decomposition into two materials (energy subtraction processing) is performed as illustrated in FIG. 7A, the noise accompanying the decomposition into two materials is reduced. On the other hand, in noise reduction processing where a filter is applied before block MD1, where decomposition into two materials is performed as illustrated in FIG. 7B, quantum noise of the X-rays is reduced. If the noise accompanying the decomposition into two materials and the quantum noise of the X-rays are independent, the noise can be further reduced by applying these instances of noise reduction processing in duplicate.

Having examined this issue, the inventors of the present application found that a standard deviation $\sigma_A$ of the accumulation image A, i.e., the quantum noise of the X-rays, and the standard deviation $\sigma_B$ of the bone image B, i.e., the noise of the bone image B, can be expressed by the following Formula (13), using a proportionality coefficient $\varepsilon_B$.

[Math 13]

$$\sigma_B^2 = \varepsilon_B \sigma_A^2 \quad (13)$$

Furthermore, the inventors of the present application found that the proportionality coefficient $\varepsilon_B$ can be approximated by Formula (14).

[Math 14]

$$\varepsilon_B \cong \frac{W\_EVEN}{W\_High}\left(\frac{\partial B}{\partial H}\right)^2 + \frac{W\_EVEN}{W\_Low}\left(\frac{\partial B}{\partial L}\right)^2 \quad (14)$$

The proportionality coefficient $\varepsilon_B$ indicates the rate of increase of noise resulting from the decomposition into two materials, and is determined by the spectrum $N_L(E)$ in low-energy X-rays, the spectrum $N_H(E)$ in high energy X-rays, the ratio of high-energy and low-energy output, the type of materials, and the like. However, the coefficient does not depend on the X-ray dose. In other words, the rate of increase in the noise accompanying the decomposition into two materials and the quantum noise of the X-rays are considered to be independent. Upon further investigations, the inventors of the present application found that the following Formula (15) is established between the standard deviation $\sigma_A(f)$ of the X-ray quantum noise at spatial frequency f (where f>0) and the standard deviation $\sigma_B(f)$ of the bone image noise at spatial frequency f (where f>0).

[Math 15]

$$\sigma_B(f)^2 = \varepsilon_B \sigma_A(f)^2 \quad (15)$$

The proportionality constant $\varepsilon_B$ in Formula (15) is constant regardless of the spatial frequency. It can therefore be said that the noise accompanying the decomposition into two materials and the X-ray quantum noise are independent at each spatial frequency f (f>0). Based on the above, it was found that there is a possibility to further reduce the noise by applying processing for reducing the noise accompanying the decomposition into two materials and processing for reducing the quantum noise of the X-rays in duplicate.

Figure 8A:
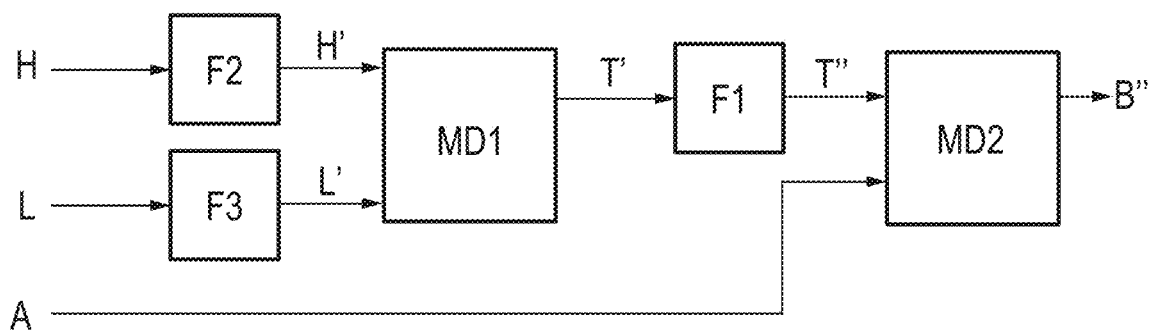
FIG. 8A is a block diagram illustrating image processing according to a first embodiment.

FIG. 8A illustrates a block diagram of the image processing according to the present embodiment. In FIG. 8A, noise reduction processing is applied to the image before decomposition into two materials and after decomposition into two materials. First, in block F2 and block F3, as in FIG. 7B, filter processing for the purpose of noise reduction is applied to the low-energy image L and the high-energy image H, respectively, which are the images from before energy subtraction processing is applied. This produces a noise-reduced low-energy image L' and a noise-reduced high-energy image H'. In block MD1, as in FIG. 7A, a noise-reduced bone image B' and a noise-reduced soft tissue image S' are obtained from the noise-reduced low-energy image L' and the noise-reduced high-energy image H'. In this manner, an image that is the sum of the noise-reduced bone image B' and the noise-reduced soft tissue image S', i.e., the noise-reduced thickness image T', is generated.

Then, block F1 applies filter processing for the purpose of noise reduction to the noise-reduced thickness image T', and a doubly noise-reduced thickness image T" is generated. Next, as in FIG. 7A, block MD2 generates a doubly noise-reduced bone image B" from the doubly noise-reduced thickness image T" and the accumulation image A. As described above with reference to FIG. 7A, a doubly noise-reduced soft tissue image S" may be generated from the doubly noise-reduced thickness image T" and the accumulation image A. Alternatively, a doubly noise-reduced soft tissue image S" may be generated from the doubly noise-reduced bone image B" and the accumulation image A. Furthermore, a doubly noise-reduced bone image B" may be generated from the doubly noise-reduced soft tissue image S" and the accumulation image A.

When noise reduction is performed in duplicate as in FIG. 8A, it is necessary to simultaneously optimize the type, strength, and the like of blocks F2 and F3 of the filter applied before block MD1, which performs the decomposition into two materials, and block F1 of the filter applied after block MD1. This is because the result of optimizing two filters independently may not be optimal. For example, if a temporal filter or a spatial filter is applied in duplicate, the quantum noise of the X-rays and the rate of increase of the noise accompanying the decomposition into two materials may no longer be independent, and the effects of the two noise reductions may not add up. Accordingly, for example, a configuration can be used in which a temporal filter is applied in blocks F2 and F3, which are filters applied before block MD1 where the decomposition into two materials is performed, and a spatial filter is applied in block F1, which is a filter applied after MD1. Naturally, a spatial filter may be applied in blocks F2 and F3, and a temporal filter may be applied in block F1.

It is also possible to employ a configuration in which either a spatial filter or a temporal filter is applied in duplicate, and in this case, it is preferable that the sizes of the kernel and the sizes of the filter coefficients for the filters are different. For example, when applying a spatial filter in duplicate, a configuration in which the kernel of the filter in block F1 is larger than the kernels in blocks F2 and F3 is preferable. This is because, for example, the thickness image T has a higher continuity in space than the accumulation image A, the high-energy image H, and the low-energy image L. When applying a temporal filter in duplicate, a configuration in which the filter coefficients of block F1 are larger than the filter coefficients of the filters in blocks F2 and F3 is preferable. This is because, for example, the thickness image T has a lower temporal change than the accumulation image A, the high-energy image H, and the low-energy image L.

A configuration may also be employed in which both a temporal filter and a spatial filter are applied in block F1, or both a temporal filter and a spatial filter are applied simultaneously in blocks F2 and F3. In either configuration, if the spatial or temporal filter is applied in duplicate before and after block MD1, where the decomposition into two materials is performed, a configuration having larger filter coefficients or kernels in block F1 of the filter after MD1 can be used.

Figure 8B:
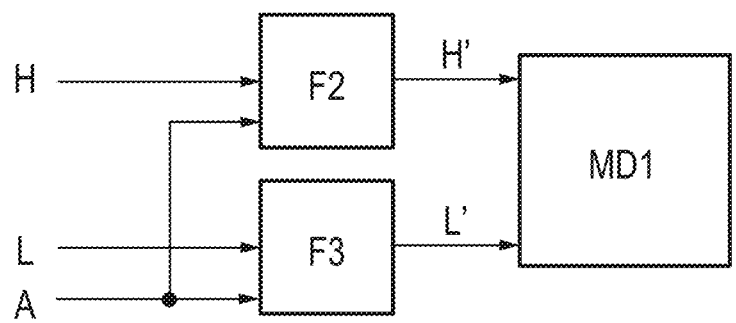
FIG. 8B is a block diagram illustrating image processing according to the first embodiment.

Furthermore, the filter processing of block F2 and block F3 may be controlled based on the accumulation image. FIG. 8B illustrates a block diagram of the image processing according to the present embodiment. In blocks F2 and F3, as in FIG. 8A, filter processing for the purpose of noise reduction is applied to the low-energy image L and the high-energy image H, respectively, and a noise-reduced low energy image L' and a noise-reduced high energy image H' are generated. For example, structure-preserving filters such as epsilon filters or Laplacian filters can be used for this filter processing. Epsilon filters and Laplacian filters can perform noise reduction while preserving the structure by determining the structure of the subject from the pixel values and changing the filter coefficients. However, there is an issue in that because the low-energy image L and the high-energy image H contain X-ray quantum noise, it is difficult to determine the noise and structure at lower doses, which in turn makes it difficult to obtain noise reduction effects. Accordingly, a configuration may be used to apply filters to the low-energy image L and the high-energy image H while changing the filter coefficients by determining the structure of the subject from the pixel values of the accumulation image A, which has less noise. For example, by controlling the noise reduction processing in block F2 and block F3 to maintain the edges of a structure detected in the accumulation image A, the edges are maintained in the low-energy image L and the high-energy image H. The processing after block MD1 is similar to that in FIG. 8A.

In FIG. 8B, the accumulation images supplied to block F2 and block F3 are the same as the accumulation image A supplied to block MD2 in FIG. 8A, but the accumulation images are not limited thereto. In other words, the accumulation images supplied to block F2 and block F3 may be different from the accumulation image A supplied to block MD2. For example, the accumulation image A generated through Formula (10) may be supplied to block MD2, and the image H of the attenuation rate at high energy may be used to control block F2 and block F3. Blocks F2 and block F3 may be different filters from each other.

As described thus far, according to the first embodiment, an increase in noise in decomposition images obtained through energy subtraction processing can be suppressed. For example, an image in which soft tissue is removed can be generated while suppressing an increase in noise in the bone image B. By displaying such an image, the visibility of contrast agents, medical devices, and the like is improved when soft tissue contrast visibility is reduced.

Although the above embodiment describes obtaining the bone image B and the soft tissue image S as the decomposition images, the decomposition images are not limited thereto. For example, the effective atomic number Z and the areal density D may be used as the decomposition images. In this case, the sum of the two decomposition images is different from the thickness image. Although the noise reduction processing for the decomposition images is performed on the sum of the decomposition images (T), the configuration is not limited thereto, and the noise reduction processing may be performed on either of the decomposition images (B or S), as described above. For example, in FIG. 8A, if the soft tissue image S' obtained in block MD1 is used, the noise-reduced bone image B" can be obtained from the accumulation image A and the noise-reduced soft tissue image S" by processing block MD2. In addition, the noise-reduced soft tissue image S" can be obtained by transforming Formula (11) using B=T−S in the processing of block MD2. In MD1, B and S are generated and T is obtained from the sum thereof, but T may be generated directly from the two energy images.

Second Embodiment

The first embodiment described a configuration in which, when the contrast of soft tissue reduces the visibility of contrast agents, medical devices, and the like, the visibility of those items is improved by removing the contrast of the soft tissue. The second embodiment will describe a configuration in which, when the contrast of bone reduces the visibility of contrast agents, medical devices, and the like, the visibility of those items is improved.

FIG. 9 illustrates an example of a soft tissue image and a thickness image. In the first embodiment, the contrast of soft tissue was removed by displaying the bone image B instead of the accumulation image A. As such, it is expected that displaying the soft tissue image S instead of the accumulation image A will make it possible to remove the bone contrast. However, upon observing the soft tissue image S of the phantom of the limbs, the inventors of the present application found that bone was visible as a reduction in soft tissue thickness, as indicated by a soft tissue image 9a in FIG. 9. This is because the thickness of the soft tissue is reduced by an amount equivalent to the thickness of the bone. When an image of the sum of the bone image B and the soft tissue image S, i.e., the thickness image T, was observed, the bone contrast was found to have disappeared and become invisible, as indicated by a bone thickness image 9b in FIG. 9. This is because the reduction in soft tissue thickness in regions where bone is present is canceled out by the addition of the bone thickness.

Upon further investigations, the inventors of the present application found that although there regions that do not contain calcium in human bones, such as cancellous bone and bone marrow, the interiors thereof are filled with organic matter (that is, not filled with gas). In other words, it can be said that the thickness of the human body when projected in one direction is continuous. Accordingly, bone contrast can be removed by displaying the thickness image T not only on the phantom but also on the human body. It should be noted that such thickness continuity may not be established in regions that can contain gas, such as the lungs and digestive organs. It should also be noted that in dried human bone phantoms, the interiors of cancellous bone, bone marrow, and the like are hollow (filled with gas), and that some organisms, such as birds, have hollow bone interiors.

Figure 10:
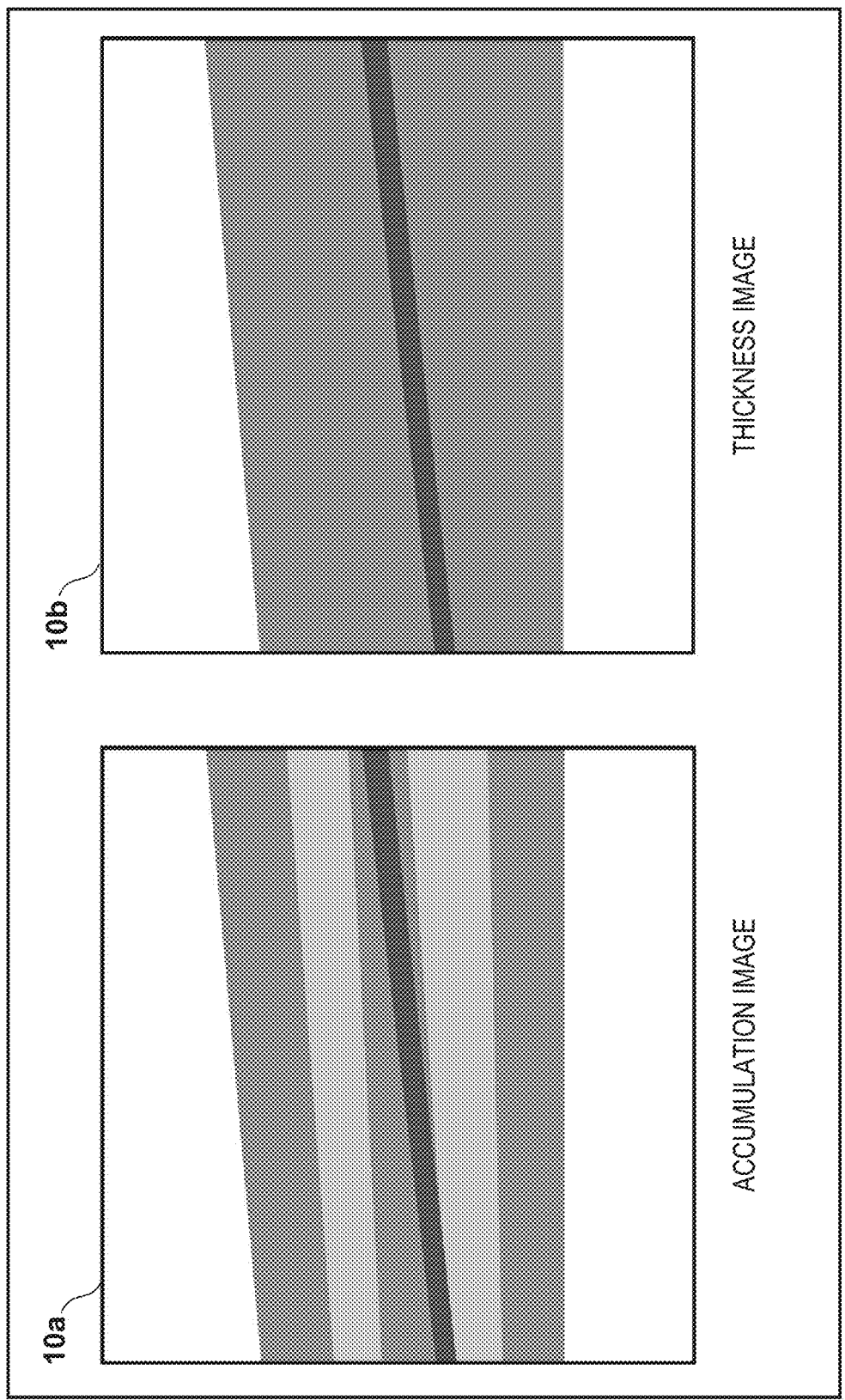
FIG. 10 is a diagram illustrating an example of an accumulation image and a thickness image.

FIG. 10 illustrates an example of an accumulation image and a thickness image. When a contrast agent is injected into the limb, the contrast of both the bone and the contrast agent is visible in the accumulation image A. This is indicated in an accumulation image 10a in FIG. 10. On the other hand, the primary component of the contrast agent is iodine, which has a higher atomic number than calcium, which is the primary component of bone. As such, the bone contrast disappears in the thickness image T, but the contrast of the contrast agent remains. This is indicated in an accumulation image 10b in FIG. 10. Accordingly, when the bone contrast reduces visibility, such as in IVR of lower extremities where the contrast agent overlaps the cortical bone portion of the femur, displaying the thickness image T in the radiation imaging system improves the visibility of the contrast agent.

However, there is a problem in that the thickness image T has more noise than the accumulation image A, which reduces the image quality. The configuration described in the first embodiment (a configuration that performs noise reduction processing in duplicate) produces a thickness image T that has undergone noise reduction processing, but in the second embodiment, noise reduction is performed on the thickness image T by combining the thickness image T with the accumulation image A.

Upon capturing images of phantoms of limbs and bony meat of animal limbs and observed the bone image B and soft tissue image S after performing decomposition into two materials as illustrated in FIG. 4B, the inventors of the present application found several characteristics.

(1) Regions with bone also have soft tissue.
(2) Many regions with soft tissue have no bone.
(3) When bone is present, the bone is of a certain thickness.

From characteristic (3), when a threshold for determining the presence or absence of bone is $B_{th}$, whether bone is present in a certain region can be determined according to whether $B_{th}$ is exceeded. In the second embodiment, noise in the thickness image T is reduced by switching processing depending on whether bone is present.

Figure 11A:
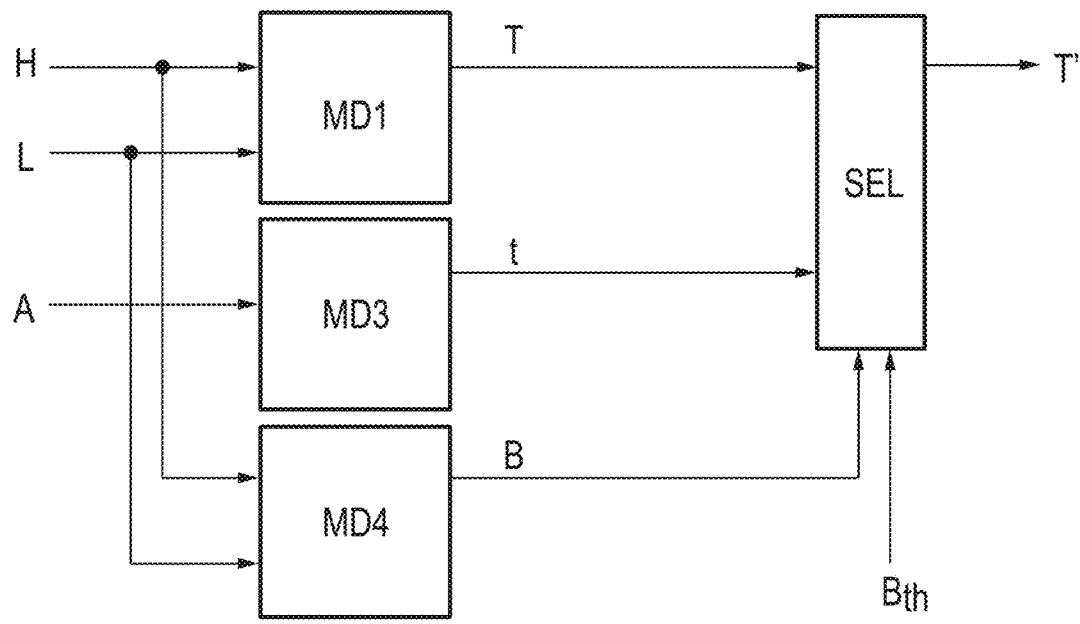
FIG. 11A is a block diagram illustrating image processing according to a second embodiment.

FIG. 11A illustrates a block diagram of the image processing according to the second embodiment. First, in block MD1, the bone image B and the soft tissue image S are obtained from the low-energy image L and the high-energy image H through a procedure similar to that in FIG. 4B, and the thickness image T is then generated by adding the bone image B and the soft tissue image S.

In block MD3, a pseudo decomposition image is generated from the accumulation image A by applying a predetermined constraint. In the present embodiment, the soft tissue image is generated as a pseudo decomposition image, using the assumption that the bone thickness is zero as a constraint. In other words, block MD3 uses the accumulation image A to generate a thickness image t, assuming that the bone thickness is 0, as indicated below. Note that the accumulation image A is as described in the first embodiment. First, Formula (16) is established by substituting B=0 and t=B+S=S into Formula (11).

[Math 16]

$$A = \frac{\int N_A(E)\exp\{-\mu_S(E)t\}EdE}{\int N_A(E)EdE} \qquad (16)$$

By substituting the pixel value of the accumulation image A at a given pixel in Formula (16) and solving the nonlinear equation, a thickness t assuming a bone thickness of 0 can be obtained. The thickness image t, which assumes that the bone thickness is 0, is originally obtained using the accumulation image A, which has low noise, and therefore has very low noise compared to the thickness image T.

In block MD4, the bone image B is generated from the low-energy image L and the high-energy image H, through a procedure similar to that in FIG. 4B. The bone image B generated in block MD1 may be used.

Block SEL determines the presence or absence of bone based on the pixel values of the bone image B, selects either the thickness image T or the thickness image t according to the result of the determination, and outputs the image as a noise-reduced thickness image T'. The thickness image T' is a combined image generated from the thickness image T and the thickness image t. In the present embodiment, if the pixel value of the bone image B generated in block MD4 exceeds the threshold $B_{th}$ for determining the presence or absence of bone, block SEL determines that bone is present, and the pixel value of the thickness image T serves as the pixel value of the thickness image T' after the noise reduction. On the other hand, if the pixel value of the bone image B is lower than the threshold $B_{th}$, block SEL determines that no bone is present, and the pixel value of the thickness image t, which assumes that the bone thickness is zero, serves as the pixel value of the thickness image T' after the noise reduction. Using the above-described configuration makes it possible to greatly reduce noise in regions where no bone is present. Also, from characteristic (2), most of the regions where soft tissue is present are regions where no bone is present. Accordingly, noise can be greatly reduced in many regions of the thickness image T'.

As described with reference to FIG. 10, the bone contrast disappears in the thickness image T (the accumulation image 10b), but the contrast of the contrast agent remains. However, when compared to the accumulation image A (the accumulation image 10a), it can be seen that there is an issue in that the contrast of the contrast agent is reduced. In addition, the thickness image T has increased noise compared to the accumulation image A. Therefore, there is a risk that the contrast of the contrast agent will be buried in noise and invisible in areas where the blood vessel diameter is small and the concentration of the contrast agent is low, such as peripheral blood vessels in the lower extremities.

According to the configuration of the second embodiment (FIG. 11A), in areas where the concentration of the contrast agent is low, such as peripheral blood vessels, the pixel value of the bone image B at the time of the decomposition into two materials is below the threshold $B_{th}$ for determining the presence or absence of bone, and it is thus determined that no bone is present. Accordingly, the pixel values of the thickness image t when the bone thickness is assumed to be 0 are selected, and the same contrast and noise as in the accumulation image A can be maintained. On the other hand, in areas where the concentration of the contrast agent is high, the pixel value of the bone image B at the time of the decomposition into two materials is above the threshold $B_{th}$ for determining the presence or absence of bone, and it is thus determined that bone is present. In this case, the pixel values of the thickness image T are selected, which may cause a drop in the contrast of the contrast agent and an increase in noise, resulting in reduced visibility compared to the accumulation image A. However, the risk of losing visibility is considered low because of the concentration of the contrast agent is high to begin with. Therefore, displaying the thickness image T' after the noise reduction improves the visibility of the contrast agent.

Figure 11B:
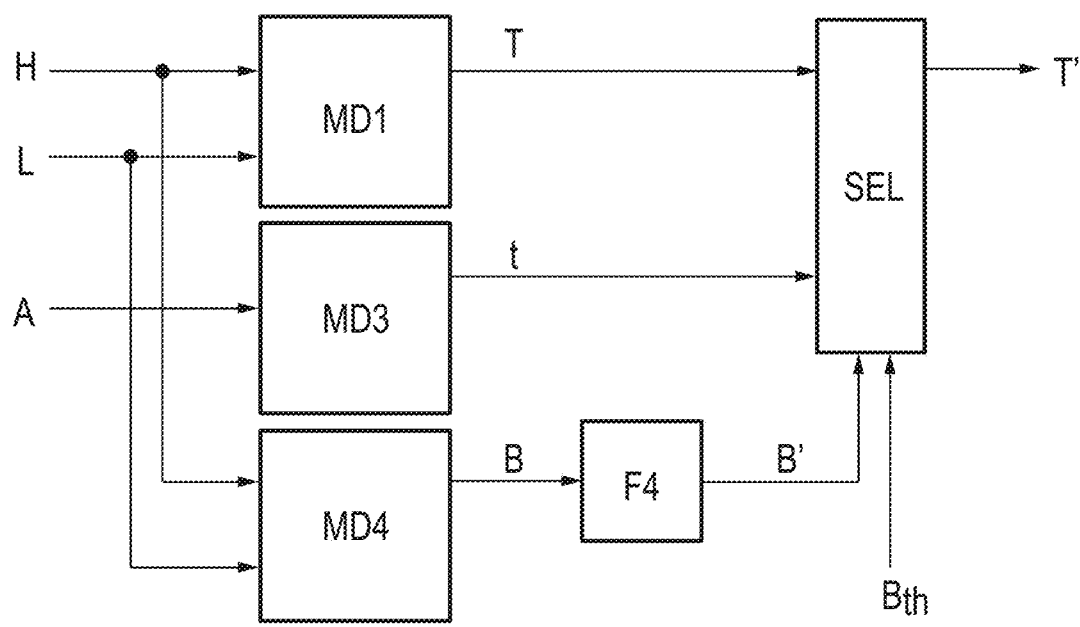
FIG. 11B is a block diagram illustrating image processing according to the second embodiment.

FIG. 11B is a block diagram illustrating another configuration of the image processing according to the second embodiment. Blocks MD1, MD3, MD4, and SEL are the same as in FIG. 11A. In the image processing of FIG. 11B, in block F4, filter processing for the purpose of noise reduction is performed on the bone image B obtained by block MD4, and the noise-reduced bone image B' is generated. For example, a spatial filter such as Gaussian and median filters, a structure-preserving spatial filter such as epsilon and Laplacian filters, and a temporal filter such as a recursive filter can be used for the filter processing. In block SEL, the noise-reduced bone image B' is input instead of the bone image B. The noise in the bone image input to block SEL is reduced, and thus the accuracy of determining the presence or absence of bone can be improved.

Figure 12:
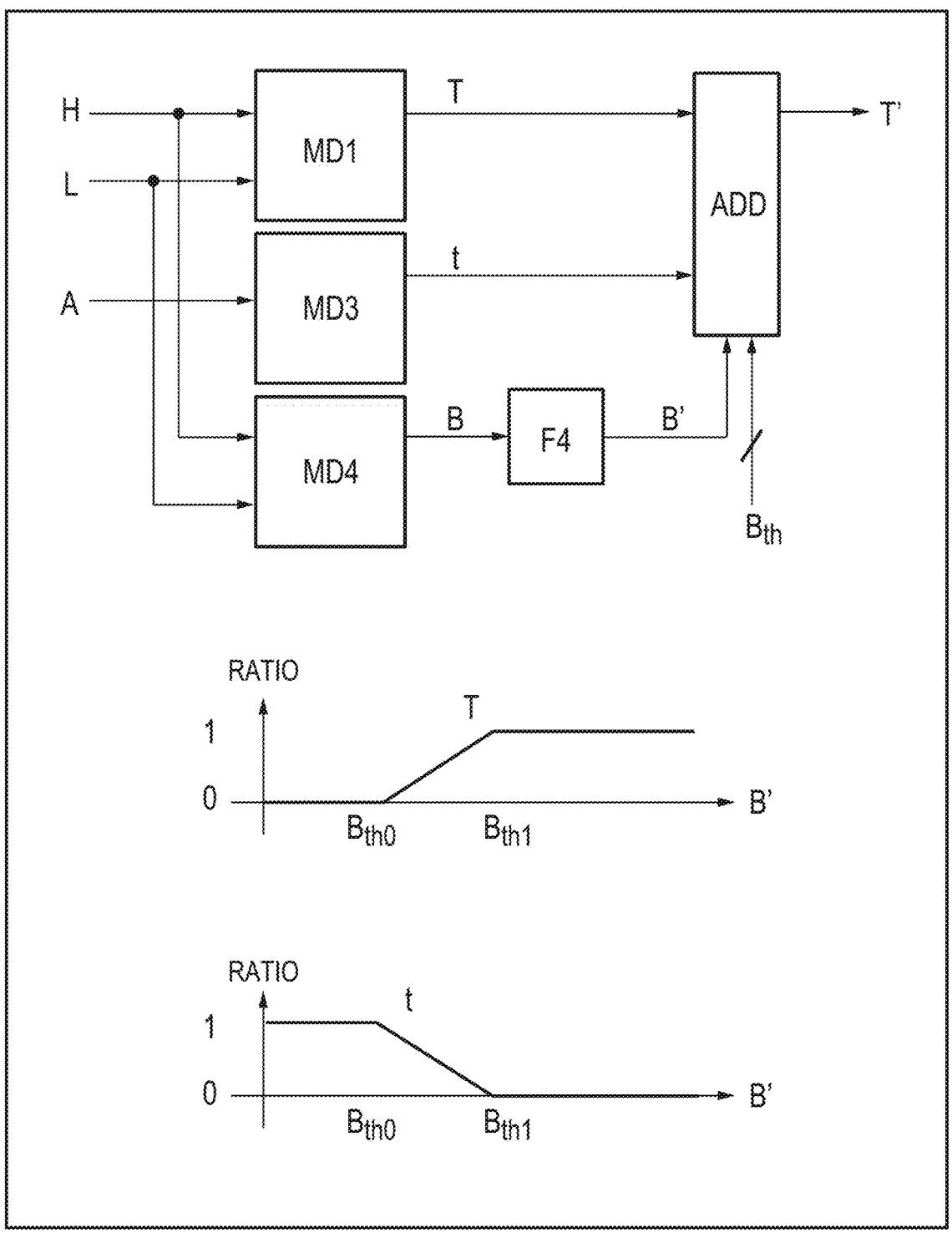
FIG. 12 is a block diagram illustrating image processing according to the second embodiment.

FIG. 12 is a block diagram illustrating yet another configuration of the image processing according to the second embodiment. Blocks MD1, MD3, MD4, and F4 are the same as in FIG. 11B. In the image processing in FIG. 12, a plurality of thresholds $B_{th}$ for determining the presence or absence of bone are set. Then, in block ADD, the pixel values of the thickness image T' after the noise reduction are determined by combining the pixel values of the thickness image T with the pixel values of the thickness image t when the bone thickness is assumed to be 0. Here, the weight of the combining (the combining ratio) is determined from the pixel values of the bone image B and the plurality of thresholds $B_{th}$ for determining the presence or absence of bone. For example, the pixel value of the thickness image T' after the noise reduction is expressed by the following Formula (17).

[Math 17]

$$T' = t \ (B' \le B_{th0}) \quad (17)$$
$$T' = \frac{B' - B_{th0}}{B_{th1} - B_{th0}} T + \frac{B_{th1} - B'}{B_{th1} - B_{th0}} t \ (B_{th0} < B' < B_{th1})$$
$$T' = T \ (B_{th1} \le B')$$

In the image processing illustrated in FIGS. 11A and 11B, the noise switches discontinuously at the boundaries of the bone, but in the image processing illustrated in FIG. 12, the noise switches continuously, which is less likely to produce a sense of unnaturalness. Although block SEL in the configuration of FIG. 11B is replaced with block ADD in FIG. 12, block SEL in FIG. 11A may be replaced with block ADD (i.e., block F4 may be omitted).

Note that in the configuration of FIG. 11A, the combining ratio of the pseudo decomposition image t in the combined image (the output of block SEL) is a first value (0) when $B > B_{th}$, and the combining ratio of the pseudo decomposition image t in the combined image is a second value (1) when $B \le B_{th}$. Here, the first value and the second value are not limited to 0 and 1, respectively, and for example, the first value may be 0.2, the second value may be 0.8, and the like. The same applies to the configuration in FIG. 11B. Additionally, in the configuration of FIG. 12, the ratio of the pseudo decomposition image t in the combined image (the output of block ADD) is changed from the first value to the second value in response to the pixel value of the bone image B' changing from a first threshold ($B_{th0}$) to a second threshold ($B_{th1}$). Here, although FIG. 12 illustrates an example in which the first value is 1 and the second value is 0, but these values are not limited thereto, and for example, the first value may be 0.8, the second value may be 0.2, and the like.

In the second embodiment, the combining ratio of the image T that combines the two decomposition images (B and S) (that is, the image of the sum) and the pseudo decomposition image t corresponding to the decomposition image (S) is determined by comparing the pixel value of the decomposition image (B) with the threshold, but the configuration is not limited thereto. For example, the combining ratio of (a) the two decomposition images and at least one image combined therewith (at least one of B, S, or T) and (b) the pseudo-image corresponding to one of the two decomposition images may be determined based on a comparison of the pixel value of at least one of the two decomposition images and a threshold.

Third Embodiment

In a third embodiment, similar to the first embodiment, in cases where soft tissue contrast reduces visibility, such as in lung field areas when performing IVR of the chest, the visibility of the contrast agent or medical device is improved by displaying the noise-reduced bone image B. In the third embodiment, a noise-reduced bone image having less noise than in the first embodiment is obtained by using the noise-reduced thickness image described in the second embodiment. Although the configuration in FIG. 12 is described in the following as an example of a configuration for generating the noise-reduced thickness image, the configurations in FIGS. 11A and 11B may be used as well.

Figure 13A:
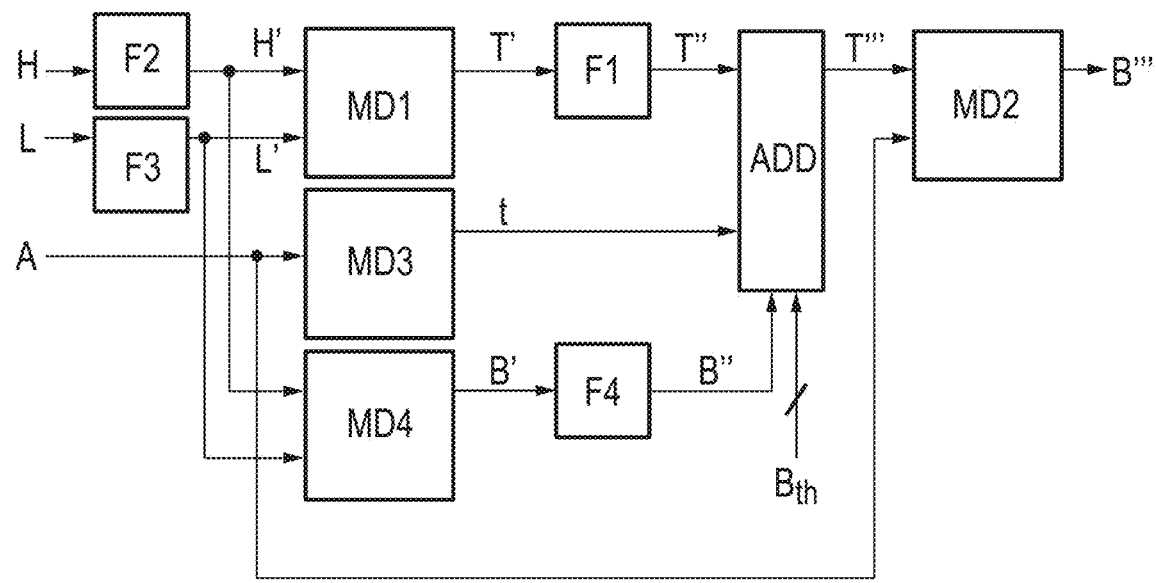
FIG. 13A is a block diagram illustrating image processing according to a third embodiment.

FIG. 13A illustrates a block diagram of the image processing according to the third embodiment. Blocks MD1, MD3, MD4, F4, and ADD are the same as in FIG. 12. Blocks F1, F2, F3, and MD2 are the same as in FIG. 8A. Accordingly, the doubly noise-reduced thickness image T''' is supplied to block ADD, resulting in a triply noise-reduced thickness image T'''. Block MD2 generates a triply noise-reduced bone image B''' by using the triply noise-reduced thickness image T'''. As a result, an image having noise reduced more than in the image processing of the first embodiment (FIG. 8A) is obtained, which further improves the visibility of contrast agents and medical devices.

Figure 13B:
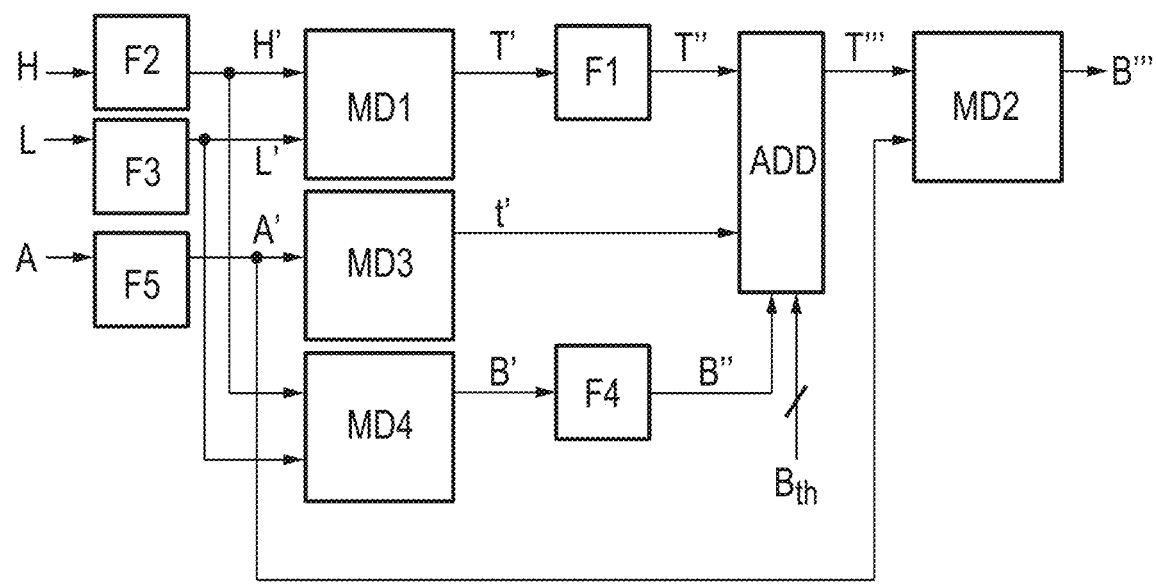
FIG. 13B is a block diagram illustrating image processing according to the third embodiment.

FIG. 13B is a block diagram illustrating another configuration of the image processing according to the third embodiment. Blocks MD1, MD3, MD4, F4, and ADD, and blocks F1, F2, F3, and MD2, are the same as in FIG. 13A. In FIG. 13B, block F5 performs filter processing for the purpose of noise reduction on the accumulation image A, and a noise-reduced accumulation image A' is generated. By inputting the noise-reduced accumulation image A' into block MD3 and block MD2 instead of the accumulation image A, noise is further reduced from the image processing in FIG. 13A, and the visibility of contrast agents and medical devices is improved.

In the first to third embodiments, processing for displaying the accumulation image A, the bone image B, the thickness image T, and the like is performed as the image processing, but the present invention is not limited to such a form. The high-energy image H, the soft tissue image S, or the like may be displayed. The image obtained as indicated by the timing chart illustrated in FIG. 3B, the image obtained from the correction illustrated in FIG. 4A, the image obtained from the image processing illustrated in FIG. 4B may also be used. Although logarithmic transformation and dynamic range compression have been described as the post-processing for these images, the present invention is not limited to such a form. A temporal filter such as a recursive filter or a spatial filter such as a Gaussian filter may be applied. In other words, the image processing in the present embodiment can be said to be processing for performing desired computations on an image after the image has been captured, corrected, or subject to image processing.

In the first to third embodiments, the X-ray imaging apparatus 104 is described as an indirect radiation sensor using a phosphor, but the apparatus is not limited to such a form. For example, a direct radiation sensors using a direct conversion material such as CdTe may be used. Additionally, in the first to third embodiments, the X-ray generation apparatus 101 passively changes the tube voltage (FIG. 3A) or actively switches the tube voltage (FIG. 3B), but the configuration is not limited to such a form. The energy of the radiation to which the X-ray imaging apparatus 104 is exposed may be varied by switching the filters of the X-ray generation apparatus 101 over time.

Furthermore, in the first to third embodiments, energy subtraction is performed by varying the energy of the radiation to which the X-ray imaging apparatus 104 is exposure, but the configuration is not limited to such a form. For example, a method may be used in which two two-dimensional detectors 106 (sensors) are stacked, which changes the spectrum of radiation detected by the front-side sensor and the rear-side sensor. A plurality of images at different energies may also be obtained by using a photon-counting sensor that counts the number of radiation quanta by energy.

In the first through third embodiments, energy subtraction processing is performed using the control computer 103 of the radiography system, but the configuration is not limited to such a form. Images obtained by the control computer 103 may be transferred to another computer, where the energy subtraction processing is performed. For example, a configuration in which obtained images are transferred to another personal computer (an image viewer) via a medical PACS, and then displayed after performing the energy subtraction processing, can be used. In other words, it is sufficient for each of the above embodiments to provide radiation images having different energies from each other for the energy subtraction processing, and the methods for obtaining radiation images having different energies from each other are not limited to those described in the above embodiments.

According to the present disclosure, noise in an image obtained by energy subtraction processing can be reduced.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a first processing unit configured to perform first noise reduction processing on a plurality of radiation images corresponding to mutually-different radiation energies;
a generating unit configured to generate a decomposition image by energy subtraction processing using the plurality of radiation images obtained by performing the first noise reduction processing; and
a second processing unit configured to perform second noise reduction processing on the decomposition image, the second noise reduction processing using a filter that differs from a filter used in the first noise reduction processing in at least one of size and type.

2. The image processing apparatus according to claim 1, wherein the first noise reduction processing and the second noise reduction processing include at least one of a spatial filter and a temporal filter, and a kernel or a filter coefficient of the filter used in the second noise reduction processing is greater than a kernel or a filter coefficient of the filter used in the first noise reduction processing.

3. The image processing apparatus according to claim 1, wherein in the first noise reduction processing, one of a spatial filter and a temporal filter is used, and in the second noise reduction processing, another of the spatial filter and the temporal filter is used.

4. The image processing apparatus according to claim 1, wherein the decomposition image is a third decomposition image obtained by combining a thickness image of a first material, the thickness image of the first material being a first decomposition image obtained from the energy subtraction processing, with a thickness image of a second material, the thickness image of the second material being a second decomposition image, and the third decomposition image is an image of a sum of a thickness of the first material and a thickness of the second material, one of the first material and the second material is bone, and another of the first material and the second material is soft tissue.

5. The image processing apparatus according to claim 1, wherein the first processing unit performs the first noise reduction processing on the plurality of radiation images such that an edge of a structure detected from a radiation image to which the energy subtraction processing is not applied is maintained.

6. The image processing apparatus according to claim 1, wherein the decomposition image is a third decomposition image obtained by combining a first decomposition image and a second decomposition image obtained from the energy subtraction processing, and the generating unit generates an image corresponding to the first decomposition image or the second decomposition image based on a radiation image to which the energy subtraction processing is not applied and the third decomposition image to which the second noise reduction processing is applied, or generates an image corresponding to the second decomposition image based on the radiation image to which the energy subtraction processing is not applied and the first decomposition image to which the second noise reduction processing is applied.

7. The image processing apparatus according to claim 1, wherein using a radiation image to which the energy subtraction processing is not applied and a predetermined constraint, the generating unit generates a pseudo decomposition image corresponding to the decomposition image obtained from the energy subtraction processing, and a combining ratio pertaining to combining of the decomposition image obtained by performing the second noise reduction processing and the pseudo decomposition image is determined using a second decomposition image obtained from the energy subtraction processing.

8. The image processing apparatus according to claim 7, wherein the generating unit generates an image corresponding to the second decomposition image based on an image obtained from the combining at the combining ratio determined and the radiation image to which the energy subtraction processing is not applied.

9. An image processing apparatus comprising:

a generating unit that generates a decomposition image by energy subtraction processing using a plurality of radiation images corresponding to mutually-different radiation energies, and generates a pseudo decomposition image using a radiation image to which the energy subtraction processing is not applied and a predetermined constraint; and a determining unit that, using the decomposition image, determines a combining ratio pertaining to combining the decomposition image and the pseudo decomposition image.

10. The image processing apparatus according to claim 9, wherein the determining unit determines a combining ratio pertaining to combining a third decomposition image, obtained by combining a first decomposition image and a second decomposition image obtained from the energy subtraction processing, with the pseudo decomposition image, using the second decomposition image.

11. The image processing apparatus according to claim 10, wherein the first decomposition image is a thickness image of a first material, and the second decomposition image is a thickness image of a second material, and the generating unit generates the pseudo decomposition image using an assumption that a thickness of the second material is 0 as the predetermined constraint.

12. The image processing apparatus according to claim 10, wherein the determining unit determines the combining ratio based on a comparison of each of pixel values in the second decomposition image with a threshold.

13. The image processing apparatus according to claim 10, wherein the determining unit determines the combining ratio to be a first value when a pixel value in the second decomposition image exceeds a predetermined threshold and determines the combining ratio to be a second value different from the first value in other cases, or changes the combining ratio from a first value to a second value different from the first value in accordance with a pixel value in the second decomposition image changing from a first threshold to a second threshold.

14. The image processing apparatus according to claim 10, further comprising:

a processing unit that applies noise reduction processing to the second decomposition image, wherein the determining unit determines the combining ratio based on the second decomposition image from after the noise reduction processing.

15. The image processing apparatus according to claim 9, wherein the plurality of radiation images are generated using a plurality of radiation images obtained by sampling and holding at a plurality of timings including during radiation emission and a timing after completion of emission, with respect to a single instance of radiation emission, and a radiation image obtained at the timing after completion of emission is used as the radiation image to which the energy subtraction processing is not applied.

16. The image processing apparatus according to claim 9, wherein the radiation image to which the energy subtraction processing is not applied is generated by weighting and combining the plurality of radiation images, or one of the plurality of radiation images is used as the radiation image to which the energy subtraction processing is not applied.

17. An image processing method comprising:

performing first noise reduction processing on a plurality of radiation images corresponding to mutually-different radiation energies;

generating a decomposition image by energy subtraction processing using the plurality of radiation images obtained by performing the first noise reduction processing; and performing second noise reduction processing on the decomposition image, the second noise reduction processing using a filter that differs from a filter used in the first noise reduction processing in at least one of size and type.

18. A non-transitory computer readable storage medium storing a program for causing a computer to execute steps in the method according to claim 17.

19. An image processing method comprising:
generating a decomposition image by energy subtraction processing using a plurality of radiation images corresponding to mutually-different radiation energies;
generating a pseudo decomposition image using a radiation image to which the energy subtraction processing is not applied and a predetermined constraint; and
determining, using the decomposition image, a combining ratio pertaining to combining of the decomposition image and the pseudo decomposition image.

20. A non-transitory computer readable storage medium storing a program for causing a computer to execute steps in the method according to claim 19.

* * * * *